United States Patent
Yu et al.

(10) Patent No.: US 10,401,321 B2
(45) Date of Patent: Sep. 3, 2019

(54) ELECTROPHORESIS APPARATUS

(71) Applicant: Coyote Bioscience Co., Ltd., Beijing (CN)

(72) Inventors: Fei Yu, Sanhe (CN); Xiang Li, Beijing (CN); Xiaobing Mu, Beijing (CN)

(73) Assignee: COYOTE BIOSCIENCE CO., LTD., Beijing (CN)

( * ) Notice: Subject to any disclaimer, the term of this patent is extended or adjusted under 35 U.S.C. 154(b) by 17 days.

(21) Appl. No.: 15/410,257

(22) Filed: Jan. 19, 2017

(65) Prior Publication Data
US 2017/0160229 A1 Jun. 8, 2017

Related U.S. Application Data

(63) Continuation of application No. PCT/CN2014/000752, filed on Aug. 6, 2014.

(51) Int. Cl.
*G01N 27/447* (2006.01)

(52) U.S. Cl.
CPC . *G01N 27/44713* (2013.01); *G01N 27/44704* (2013.01); *G01N 27/44747* (2013.01)

(58) Field of Classification Search
CPC ....... G01N 27/44713; G01N 27/44747; G01N 27/447–453
See application file for complete search history.

(56) References Cited

U.S. PATENT DOCUMENTS

2008/0142365 A1* 6/2008 Kober .............. G01N 27/44726
204/450

FOREIGN PATENT DOCUMENTS

| CN | 101614695 A | 12/2009 |
|---|---|---|
| CN | 102656448 A | 9/2012 |
| EP | 2587257 A1 | 5/2013 |
| GB | 2302590 A | 1/1997 |
| WO | WO-0120315 A1 | 3/2001 |
| WO | WO-2006082575 A1 | 8/2006 |
| WO | WO-2014058462 A1 | 4/2014 |
| WO | WO-2016/019482 A1 | 2/2016 |

OTHER PUBLICATIONS

"How a car works: How a car electrical system works", URL: https://www.howacarworks.com/basics/how-car-electrical-systems-work, downloaded Jun. 20, 2018; published on Nov. 24, 2013.*
International search report and written opinion dated May 6, 2015 for PCT Application No. CN2014/000752.

* cited by examiner

*Primary Examiner* — J. Christopher Ball
(74) *Attorney, Agent, or Firm* — Wilson Sonsini Goodrich & Rosati

(57) ABSTRACT

Provided herein are devices, systems, and methods for conducting electrophoresis. The devices, systems, and methods are suited for portability, low power consumption, integrated operation, and remote monitoring.

24 Claims, 38 Drawing Sheets

ELECTROPHORESIS APPARATUS

CROSS-REFERENCE

This application is a continuation of PCT International Application Serial No. PCT/CN2014/000752, filed Aug. 6, 2014, which application is incorporated herein by reference.

BACKGROUND

Gel electrophoresis is a technique used to separate and analyze samples, such as DNA, RNA, and proteins, based on their size and/or electrical charge. Sample molecules, such as DNA, can be moved through a gel under the influence of an electric field. Samples can be loaded into a gel and placed inside an electrophoresis chamber, which can be connected to a power source to generate an electric field.

A molecule's rate of migration through the gel can depend on several factors, including the length, conformation, and charge of the molecule as well as the type and porosity of the gel. Nucleic acids are commonly separated in agarose gels. In this situation, shorter molecules can move faster, and therefore migrate farther over a given time, through the pores of the gel. This process is called sieving. In other situations, for example the separation of proteins in agarose, the gel pores may be too large to sieve the molecules. Proteins are commonly separated in polyacrylamide gels, either in their native state or after denaturing. The electrophoretic mobility of a native protein can depend on the length, charge, and conformation of the protein. The electrophoretic mobility of a denatured protein can depend on its length and its mass-to-charge ratio. In some cases, proteins can be denatured using sodium dodecyl sulfate (SDS), which linearizes and negatively charges proteins. This results in an even distribution of charge per mass, which can result in a separation approximately by size alone.

SUMMARY

A need exists for improved systems and methods for electrophoresis. Low power electrophoresis may be provided, wherein the low power electrophoresis may operate at a low voltage. Such low power electrophoresis may permit electrophoresis apparatuses to be portable and operable in different situations. For example, the electrophoresis apparatuses may be taken out into the field or into portions of the country where regular power sources are not readily available. The use of low voltage power may also permit the electrophoresis apparatus to be charged in transit or be charged by power sources that may otherwise not be able to accommodate traditional electrophoresis devices. These features can greatly improve the ability to perform electrophoresis in different point-of-care (POC) settings.

Integrated real-time electrophoresis may occur. A detector may be provided as part of an electrophoresis apparatus. A detector can provide imaging of the electrophoresis matrix before, during, and/or after operation. A detector can provide still images or video of an electrophoresis matrix. A detector can image the entirety or majority of a matrix in one frame. Images and videos from a detector can be used to analyze the results of an electrophoretic separation. Images and videos from a detector can advantageously be used to monitor the progress of an electrophoretic separation.

An electrophoresis apparatus or an associated detector can comprise communication equipment. Communication equipment can transmit information from the apparatus and/or detector, such as imaging data (e.g., images or videos) or operational data (e.g., voltage, field strength, run time). Communication equipment can be used to provide instructions to the apparatus and/or detector, such as instructions to begin electrophoresis, stop electrophoresis, alter the applied voltage or electric field strength, take an image or video, transmit an image or video, begin taking images or videos at a specified time or rate, or stop taking images or videos. Instructions can be given to be carried out immediately or at a future time. Thus, remote monitoring and/or control of electrophoresis may occur.

Electrophoresis may occur in separated lanes. The matrix can comprise physical dividers to separate lanes for electrophoresis. Such dividers can prevent cross-contamination or migration of samples between lanes. Such dividers can also allow for the simultaneous use of multiple types of matrix. For example, gels of different porosities can be placed into different lanes, allowing samples with analytes of different size ranges to be separated with better resolution than if the sample were separated using a single porosity of gel. Lanes can be separated side-to-side but still open on top, allowing an optical path to a detector for imaging.

An aspect of the present disclosure provides an apparatus for performing electrophoresis on a sample comprising: a frame comprising a bottom plate and a plurality of side walls; an electrophoresis gel retained in said frame; and an electrical component that produces an electric field through the electrophoresis gel to cause at least a portion of the sample to migrate through the gel, wherein the electrical component is powered by no more than 12 V.

In an embodiment, the apparatus further comprises a housing within which the frame, the electrophoresis gel, and the electrical component are contained.

In an embodiment, the housing prevents external light from entering the housing.

In an embodiment, a light source is provided within the housing.

In an embodiment, power both for the electrical component and for the light source is provided by no more than one power cable.

In an embodiment, the electrophoresis gel comprises at least one well configured to receive the sample.

In an embodiment, the apparatus further comprises a power connector configured to electrical connect the apparatus to an external power source.

In an embodiment, the external power source provides no more than 12 V.

In an embodiment, the external power source is an off-grid power source.

In an embodiment, the external power source is a motor vehicle.

In an embodiment, the motor vehicle provides power to the power connector via a charging port of the motor vehicle.

In an embodiment, the charging port is a cigarette lighter receptacle of the motor vehicle.

In an embodiment, the motor vehicle provides power to the power connector from a battery of the motor vehicle.

In an embodiment, the motor vehicle provides power to the power connector while the vehicle is in operation.

In an embodiment, the motor vehicle provides power to the power connector while the vehicle is in motion.

In an embodiment, a method of performing electrophoresis comprises performing electrophoresis using the apparatus.

In an embodiment, the method of performing electrophoresis further comprises powering the apparatus using no more than about 12 V.

In an embodiment, the method of performing electrophoresis further comprises monitoring the electrophoresis in real time over a wireless connection.

An aspect of the present disclosure provides an apparatus for performing electrophoresis on a sample comprising: a frame comprising a bottom plate and a plurality of side walls and a least one lane separator; and an electrophoresis gel retained in said frame, wherein the lane separator separates at least a portion of the electrophoresis gel from another portion of the electrophoresis gel into multiple lanes and inhibits transport of sample material between adjacent lanes during the electrophoresis, wherein top surfaces of the electrophoresis gel in the multiple lanes are in fluid communication with one another.

An aspect of the present disclosure provides an apparatus for performing electrophoresis on a sample comprising: a frame comprising a bottom plate and a plurality of side walls and at least one lane separator; and an electrophoresis gel retained in said frame, wherein the lane separator separates at least a portion of the electrophoresis gel from another portion of the electrophoresis gel into multiple lanes and inhibits transport of sample material between adjacent lanes during the electrophoresis, wherein the electrophoresis gel in the multiple lanes have top surfaces that are exposed to a space.

In an embodiment, the apparatus further comprises an electrical component that produces an electric field through the electrophoresis gel to cause at least a portion of the sample to migrate through the electrophoresis gel.

In an embodiment, the electrical component comprises a plurality of electrodes.

In an embodiment, the electric field causes at least a portion of the sample to migrate through the electrophoresis gel in a first lane of the multiple lanes, and at least a portion of the sample to migrate through the electrophoresis gel in a second lane of the multiple lanes.

In an embodiment, the lane separator is substantially parallel to at least one side wall.

In an embodiment, the lane separator comprises a connector region, through which at least some of the sample material can be transported between adjacent lanes.

In an embodiment, the electrophoresis gel in a first lane of the multiple lanes varies in composition from the electrophoresis gel in a second lane of the multiple lanes.

In an embodiment, the frame comprises a plurality of lane separators that are substantially parallel to one another.

In an embodiment, the lane separators are formed from a solid material.

In an embodiment, the lane separators are integrally formed with the bottom plate of the frame wherein the top surfaces of the electrophoresis gel in the multiple lanes are exposed to a space that permits the top surfaces to be in fluid communication with one another.

In an embodiment, the apparatus further comprises a detector configured to detect a signal from the electrophoresis gel while the electric field is produced through the electrophoresis gel.

In an embodiment, the detector is housed in a top slide panel of the apparatus.

In an embodiment, the signal is an optical signal.

In an embodiment, the detector is configured to detect the signal from the electrophoresis gel in the multiple lanes simultaneously.

In an embodiment, the detector is configured to image the electrophoresis gel from the multiple lanes simultaneously.

In an embodiment, the detector communicates wirelessly with an external device.

In an embodiment, the external device is configured to display an image captured by the detector in real-time.

An aspect of the present disclosure provides an apparatus for performing electrophoresis on a sample comprising: a frame comprising a bottom plate and a plurality of side walls; an electrophoresis gel retained in said frame; and an electrical component that produces an electric field through the electrophoresis gel to cause at least a portion of the sample to migrate through the gel, wherein the apparatus has (1) a greatest lateral dimension of no more than 15 cm, or (2) a height of no more than 30 cm.

In an embodiment, the apparatus further comprises a housing configured to enclose the frame, electrophoresis gel, and the electrical component, wherein the housing has a greatest lateral dimension of no more than 15 cm.

In an embodiment, the apparatus is configured to perform electrophoresis in at least 8 different regions simultaneously.

In an embodiment, the apparatus further comprises a housing configured to enclose the frame, electrophoresis gel, and the electrical component, wherein the housing has a height of no more than 30 cm.

In an embodiment, the apparatus is configured to perform electrophoresis in at least 8 different regions simultaneously.

In an embodiment, a ratio of the height to the greatest lateral dimension is no more than one.

In an embodiment, a ratio of the height to the greatest lateral dimension is greater than one.

In an embodiment, the apparatus weighs no more than about 1 kg.

In an embodiment, the total apparatus volume is less than about 3500 $cm^3$.

In an embodiment, the apparatus footprint is less than about 250 $cm^2$.

An aspect of the present disclosure provides an apparatus for performing electrophoresis on a sample comprising: a frame comprising a bottom plate and a plurality of side walls; an electrophoresis gel retained in said frame; an electrical component that produces an electric field through the electrophoresis gel to cause at least a portion of the sample to migrate through the gel; and a detector configured to detect a signal from the electrophoresis gel while the electric field is produced through the electrophoresis gel, wherein the apparatus comprises a housing within which the frame, the electrophoresis gel, the electrical component, and the detector are contained.

In an embodiment, the housing prevents external light from entering the housing.

In an embodiment, a light source is provided within the housing.

In an embodiment, the detector is configured to detect a signal from the electrophoresis gel while the portion of the sample is migrating through the gel.

In an embodiment, the signal is an optical signal.

In an embodiment, the detector comprises an imaging device configured to capture an image of the electrophoresis gel.

In an embodiment, the detector is configured to capture an image of the entire electrophoresis gel in the frame simultaneously.

In an embodiment, the detector is a wide angle camera.

In an embodiment, the detector communicates wirelessly with an external device.

In an embodiment, the external device is configured to display an image captured by the detector in real-time.

In an embodiment, the external device includes a processor that runs a program to remove a fishbowl effect from data captured by the detector.

In an embodiment, the frame is a tray configured to move relative to the detector.

In an embodiment, the tray is configured to slide laterally relative to the detector.

In an embodiment, the tray is configured to move between an open position where the electrophoresis gel is exposed to the external environment and a closed position where the electrophoresis gel is within a housing of the apparatus.

In an embodiment, the apparatus has a height of no more than 30 cm.

In an embodiment, the apparatus has a weight of no more than about 1 kg.

In an embodiment, the total apparatus volume is less than about 3500 $cm^3$.

In an embodiment, the apparatus footprint is less than about 250 $cm^2$.

An aspect of the present disclosure provides an apparatus for performing electrophoresis on a sample comprising: a frame comprising a bottom plate and a plurality of side walls; a plurality of test regions within the frame, each test region comprising an electrophoresis gel of a different porosity; an electrical component that produces an electric field through the electrophoresis gel in the plurality of test regions to cause at least a portion of the sample to migrate through the gel.

In an embodiment, the frame comprises at least one lane separator that separates the plurality of test regions into separate lanes.

In an embodiment, each of the test regions in the separate lanes includes a sample loading region configured to receive a sample.

In an embodiment, the sample loading region includes a well in the electrophoresis gel configured to receive the sample.

In an embodiment, the sample loading regions of the separate lanes are configured to simultaneously receive a sample from a multi-headed pipette.

In an embodiment, the width between the separate lanes and heads of the multi-headed pipette are substantially the same.

In an embodiment, the electrophoresis gel in the plurality of test regions comprise molecules embedded and/or separated therein having a molecular weight that differs by at least three orders of magnitude between the plurality of test regions.

In an embodiment, the molecules are nucleic acids of 10 b to 10 kb.

In an embodiment, the porosities of the electrophoresis gels in the different test regions differ by at least 1 order of magnitude.

An aspect of the present disclosure provides a method for performing electrophoresis on a sample, comprising: providing an electrophoresis apparatus as provided in other aspects of the present disclosure; loading sample into the electrophoresis gel; and producing an electric field to cause at least portions of the sample to migrate through the electrophoresis gel.

In an embodiment, the method further comprises controlling operation of the apparatus by transmitting instructions to the apparatus from a remote device.

In an embodiment, the method further comprises transmitting operating condition data from the apparatus to a remote device.

In an embodiment, the method further comprises transmitting images or video of the gel to a remote device.

In an embodiment, transmitting is performed wirelessly.

In an embodiment, transmitting images or video is performed in real-time.

In an embodiment, the method further comprises providing power to the apparatus via at most one power cable.

An aspect of the present disclosure provides a method for performing electrophoresis on a sample, said method comprising: providing a plurality of test regions, each test region comprising an electrophoresis gel; and producing an electric field through the electrophoresis gel in the plurality of test regions to cause at least portions of the sample to migrate through the electrophoresis gel in the plurality of test regions, wherein the electric field causes the electrophoresis gel in the plurality of test regions to embed and/or separate molecules having a molecular weight that differs by at least three orders of magnitude between the plurality of test regions.

In an embodiment, the plurality of test regions are provided within a frame having a bottom plate and a plurality of side walls.

In an embodiment, the frame has at least one lane separator dividing the plurality of test regions from one another.

In an embodiment, the electrophoresis gel of each test region is of a different porosity.

In an embodiment, the porosities of the electrophoresis gels in the different test regions differ by at least 1 order of magnitude.

In an embodiment, the molecules are nucleic acids of 10 b to 10 kb.

In an embodiment, the method further comprises capturing an image of the electrophoresis gel while the electric field is produced through the electrophoresis gel.

In an embodiment, the method further comprises transmitting the image of the electrophoresis gel to an external device.

In an embodiment, the method further comprises, prior to producing the electric field, loading at least a portion of a sample into a first well of an electrophoresis gel of a first test region, and loading at least a portion of a sample into a second well of an electrophoresis gel of a second test region.

An aspect of the present disclosure provides a method for monitoring electrophoresis of a sample, said method comprising: producing an electric field through an electrophoresis gel to cause at least a portion of the sample to migrate through the electrophoresis gel; and capturing an image of the electrophoresis gel while the electric field is produced through the electrophoresis gel; and transmitting the image of the electrophoresis gel to an external device located at a separate facility from the electrophoresis gel.

In an embodiment, the image is transmitted wirelessly.

In an embodiment, the image is transmitted to the external device while the electric field is produced.

In an embodiment, the image is transmitted to the external device in real-time.

In an embodiment, the image is captured with aid of a camera that is within a housing that encloses the camera and the electrophoresis gel.

In an embodiment, the housing has a height of no more than 30 cm.

In an embodiment, the housing has a greatest lateral dimension of no more than 15 cm.

In an embodiment, the external device is a computer.

In an embodiment, the external device is a handheld mobile device.

In an embodiment, the method further comprises receiving, from the external device, one or more commands that affect the electric field through the electrophoresis gel.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
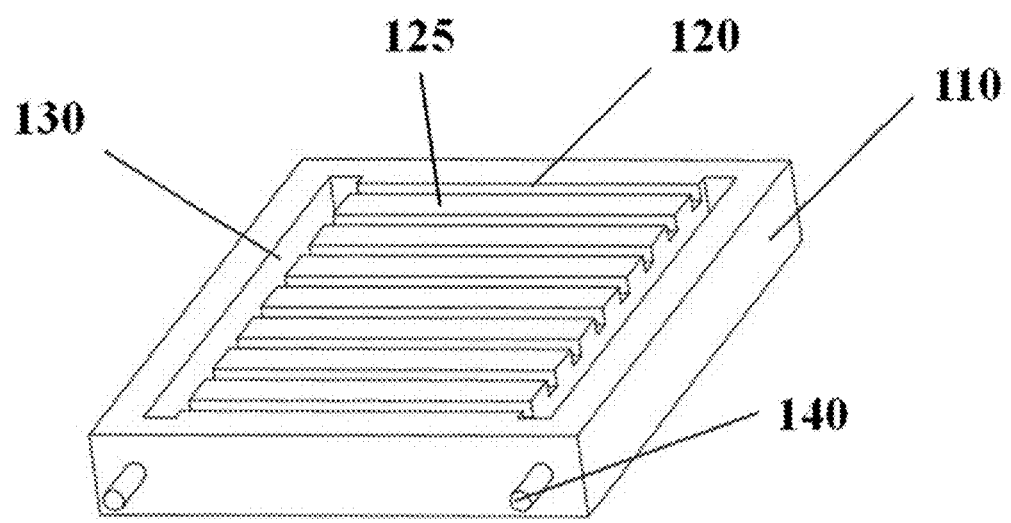
FIG. 1 shows an exemplary three-quarters view schematic of a multi-lane electrophoresis apparatus.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention provides systems and methods for electrophoresis. Various aspects of the invention described herein may be applied to any of the particular applications set forth below or for any other types of separation systems. The invention may be applied as a standalone system or method, or as part of an integrated sample processing system. It shall be understood that different aspects of the invention can be appreciated individually, collectively, or in combination with each other.

The term "about" or "nearly" as used herein refers to within +/−10%, 9%, 8%, 7%, 6%, 5%, 4%, 3%, 2%, or 1% of the designated amount.

The present disclosure provides apparatuses for electrophoresis. Electrophoresis involves the migration of species in a sample through a matrix or medium, such as a gel, in the presence of an electric field. The terms matrix and gel may be used interchangeably in this disclosure. The physical properties of the matrix and of the sample species can affect the rate of migration, allowing separation of different species within a sample. Relevant physical properties of sample species include size, electrical charge, and conformation. Electrophoresis can be conducted within an apparatus, which can provide a matrix (e.g., a gel), buffer solution, and electrodes for generating an electric field.

The electrophoresis apparatuses provided for in this disclosure can be well-suited for portability and field operation. The apparatuses can be designed to run on a low voltage power source, such as a motor vehicle power adaptor, and can have integrated power supply circuitry. The apparatuses can run directly from a low voltage power source or can run from energy storage devices (e.g., batteries) charged from a low voltage power source. This affords portability and the ability to process samples in remote locations. The apparatuses can comprise physical barriers between the lanes of the matrix, preventing contamination between samples. The physical barriers may also permit variability in the gels used in each of the lanes or types of molecules detected within the lanes. Detectors, such as cameras, can be coupled or mounted to the apparatuses, or can be integrated into the apparatuses. Communications equipment, wired (e.g. USB) or wireless (e.g., Wi-Fi), can be integrated into the apparatuses or detectors to facilitate remote monitoring and control of the operation.

Figure 2A:
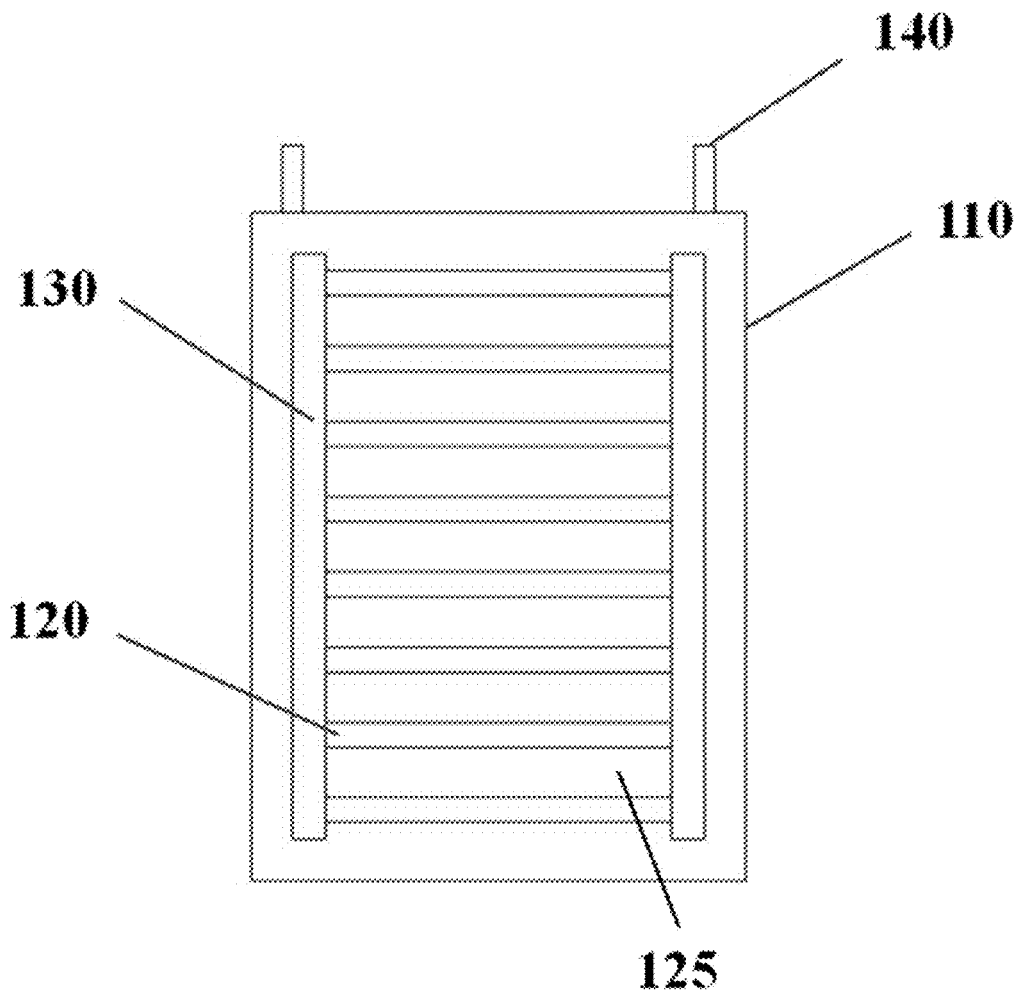
FIG. 2A shows an exemplary top-down view schematic of a multi-lane electrophoresis matrix.
Figure 2B:
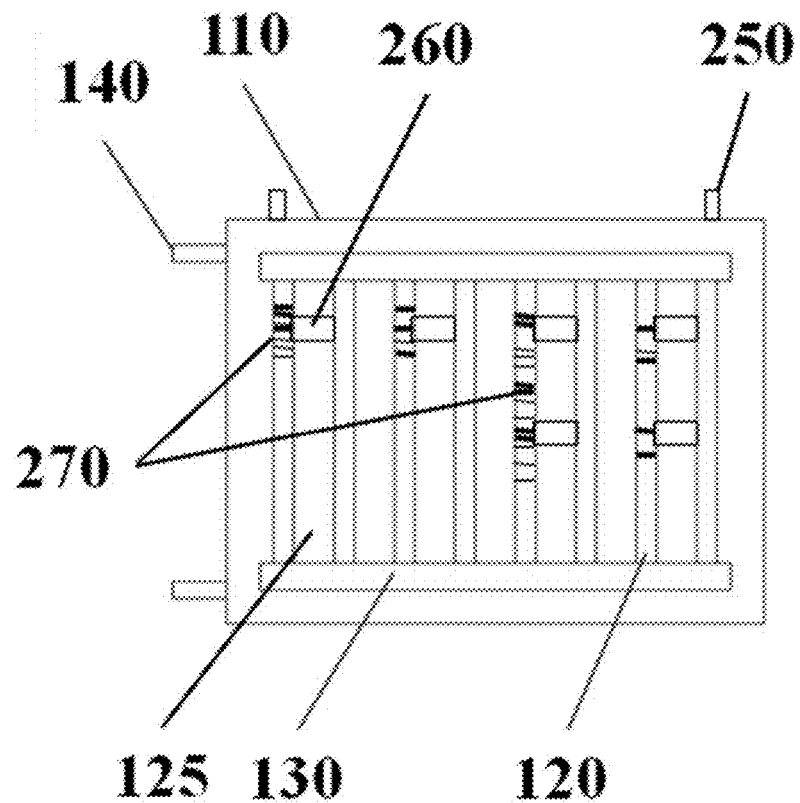
FIG. 2B shows an exemplary top-down view schematic of a multi-lane electrophoresis matrix with multiple sets of electrodes and connectors between lanes.
Figure 2C:
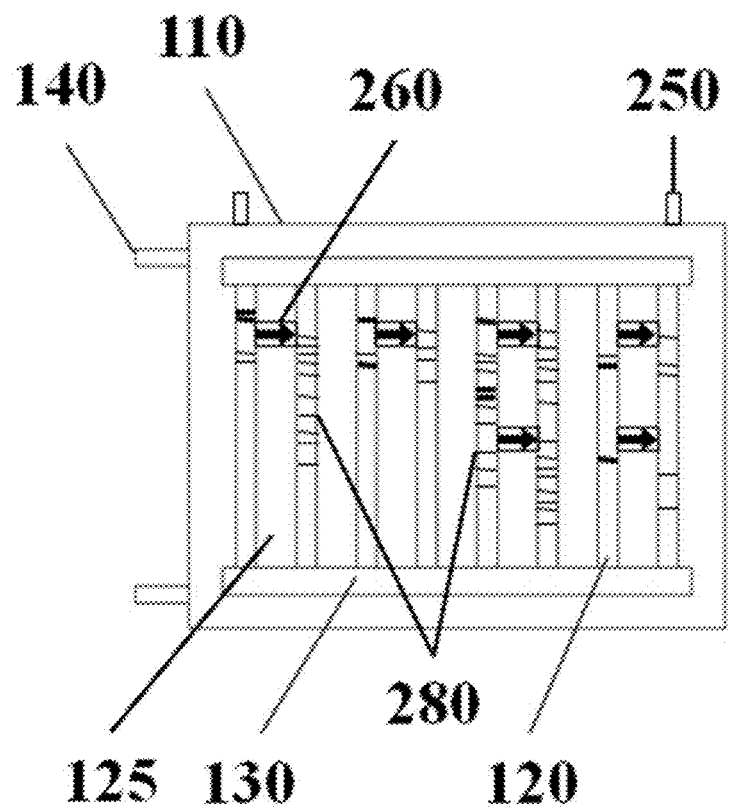
FIG. 2C shows an exemplary top-down view schematic of a multi-lane electrophoresis matrix with multiple sets of electrodes and connectors between lanes.
Figure 3:
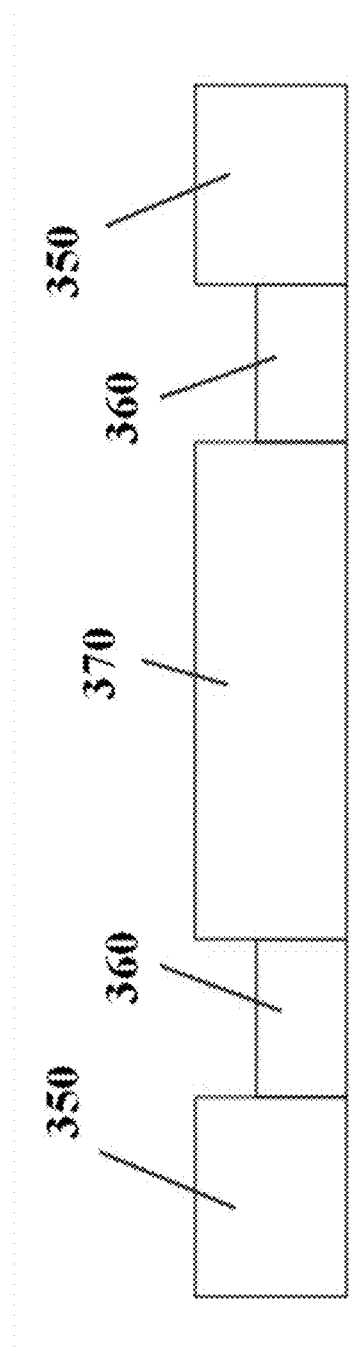
FIG. 3 shows an exemplary side view schematic of a multi-lane electrophoresis apparatus.

FIG. 1 and FIG. 2A show a schematic of an electrophoresis separation matrix 110, from three-quarters and top-down views, respectively. The electrophoresis matrix can comprise gel lanes or channels 120. Physical barriers 125 can be located between samples running in neighboring gel lanes or channels. The electrophoresis matrix can comprise troughs or chambers 130 for holding buffer or other fluids. The electrophoresis matrix can comprise electrodes 140. FIG. 2B and FIG. 2C show schematics of electrophoresis matrices with additional electrodes 250 oriented in a different direction from the first electrodes 140. These electrophoresis matrices can also comprise connectors 260 between gel lanes. Samples, such as DNA, with larger size or with smaller size can be directed into different gel lanes via the connectors. The gel lanes into which these samples are directed can comprise gel composed to provide higher resolution for the selected samples, such as gels with higher or lower densities. Markers 270, 280 can be included as a reference for different sample sizes or lengths, such as for longer lengths 270 and shorter lengths 280. FIG. 3 shows a side-view schematic of a gel lane, with electrodes 350 positioned on the ends, and with buffer 360 positioned between the electrodes and the gel 370.

Figure 4:
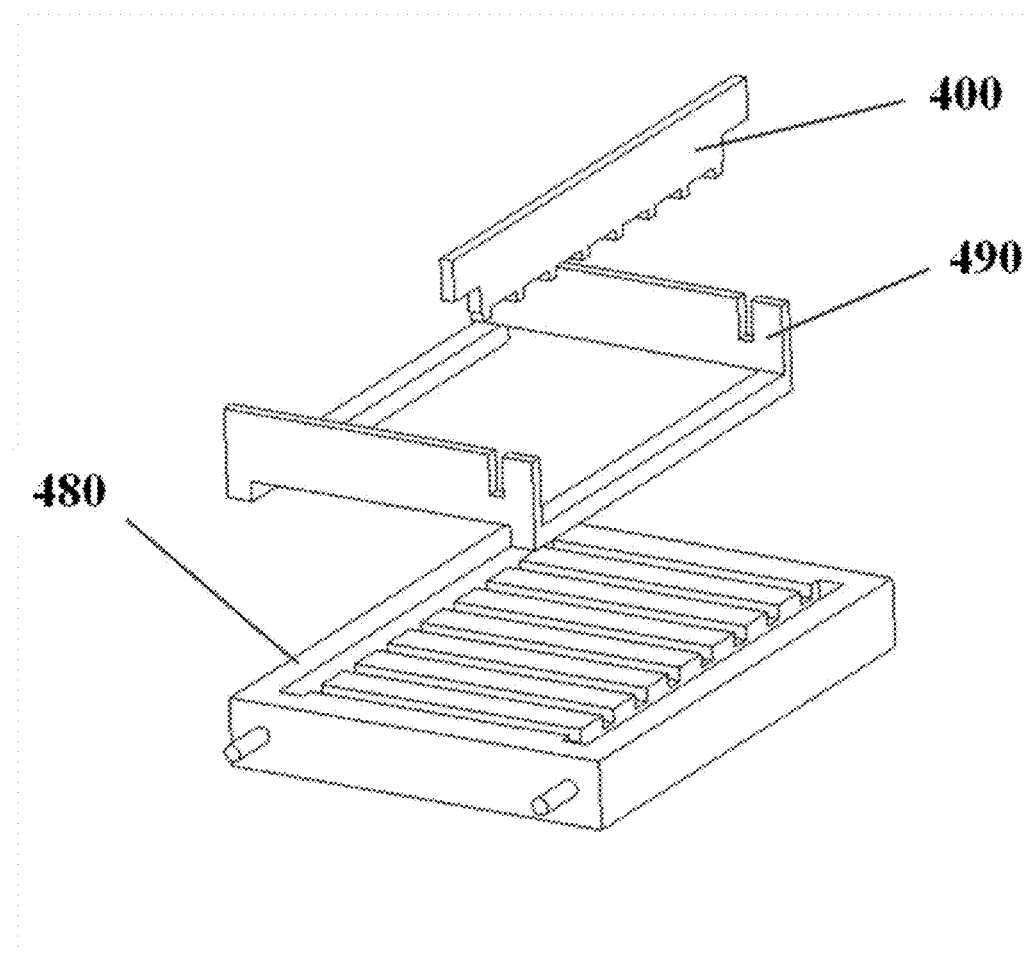
FIG. 4 shows an exemplary schematic of a lane electrophoresis apparatus with a gel casting frame and comb.
Figure 5:
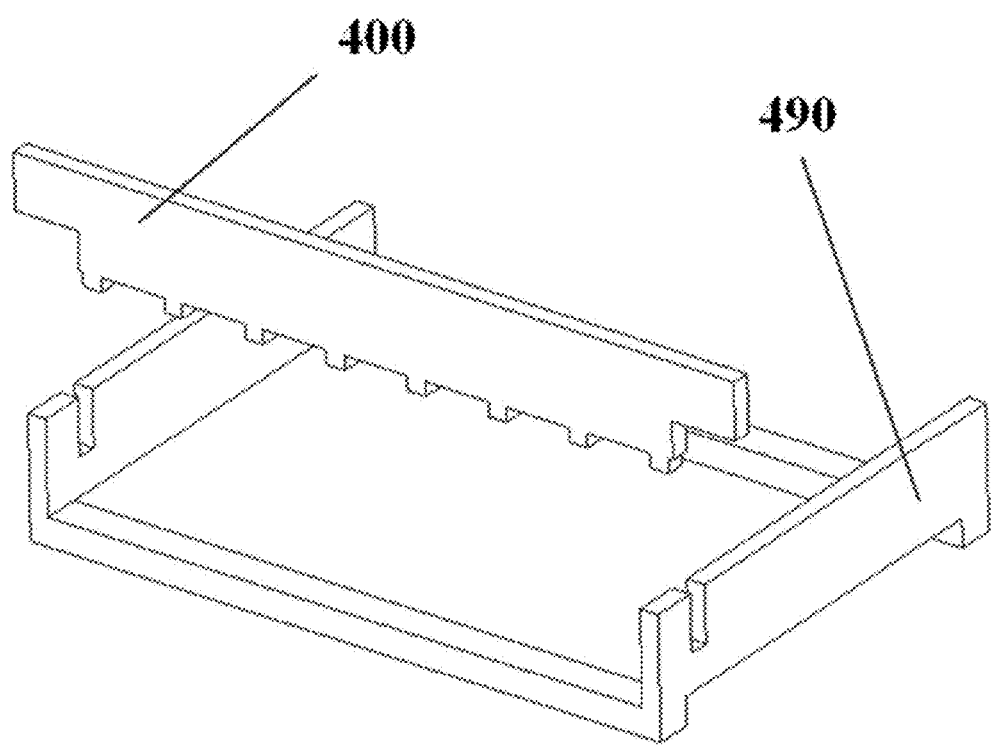
FIG. 5 shows an exemplary schematic of a gel casting frame and comb.

Gel can be cast in a lane electrophoresis apparatus 480 with the aid of a gel casting frame 490 and a comb 400, as shown for example in FIG. 4 and FIG. 5. The comb can be used to form wells in the gel for loading sample before the gel solidifies. Electrophoresis gel, for example in liquid form, can be added to a lane electrophoresis apparatus 480 or gel casting frame 490 with the aid of a pump, such as an auto pipette 610 with associated pipette tips 620, as shown for example in FIG. 6. In some cases, the buffer chamber can be filled with buffer prior to adding liquid gel to the lanes, in order to avoid contact between the liquid gel and the electrode. A pump, such as an auto pipette, can also be used for loading samples into wells.

Figure 7:
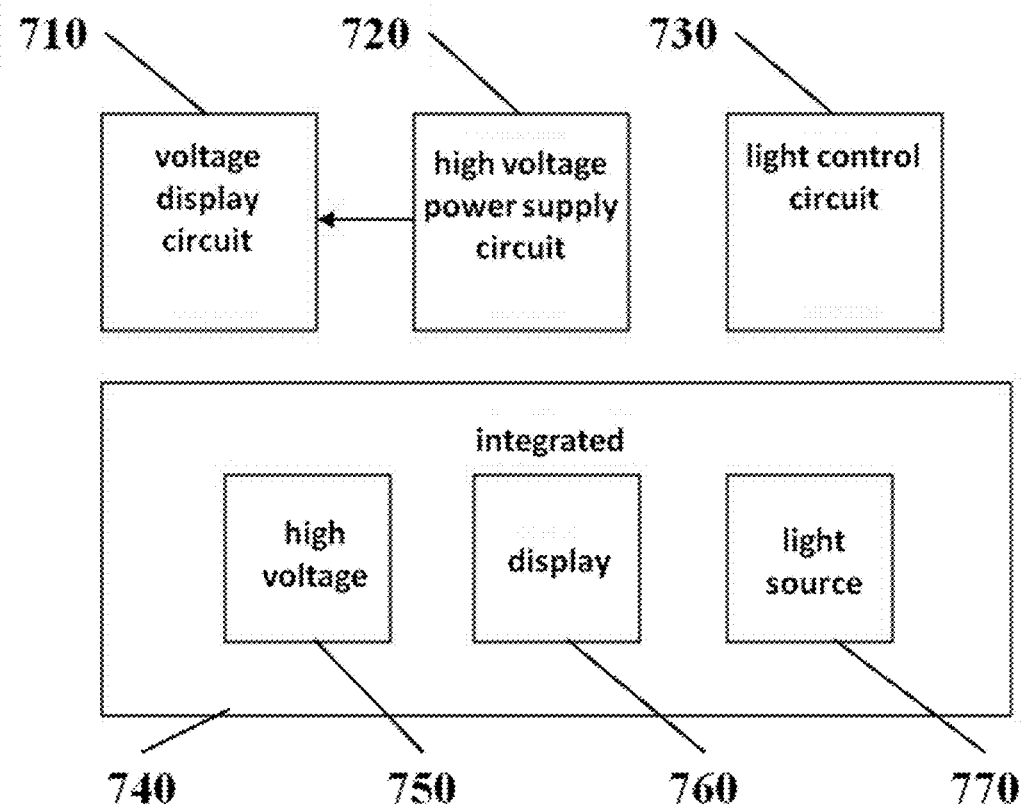
FIG. 7 shows an exemplary schematic of a circuit composition for an electrophoresis apparatus.

Electrophoresis apparatuses can comprise voltage display circuits 710, which can display voltage information from a high voltage power supply circuit 720, as shown in FIG. 7. Apparatuses can also comprise light control circuits 730. Circuits can be used in the control of an integrated apparatus or system 740, comprising a high voltage source 750, a display 760, and a light source 770 in one integrated system.

Figure 8:
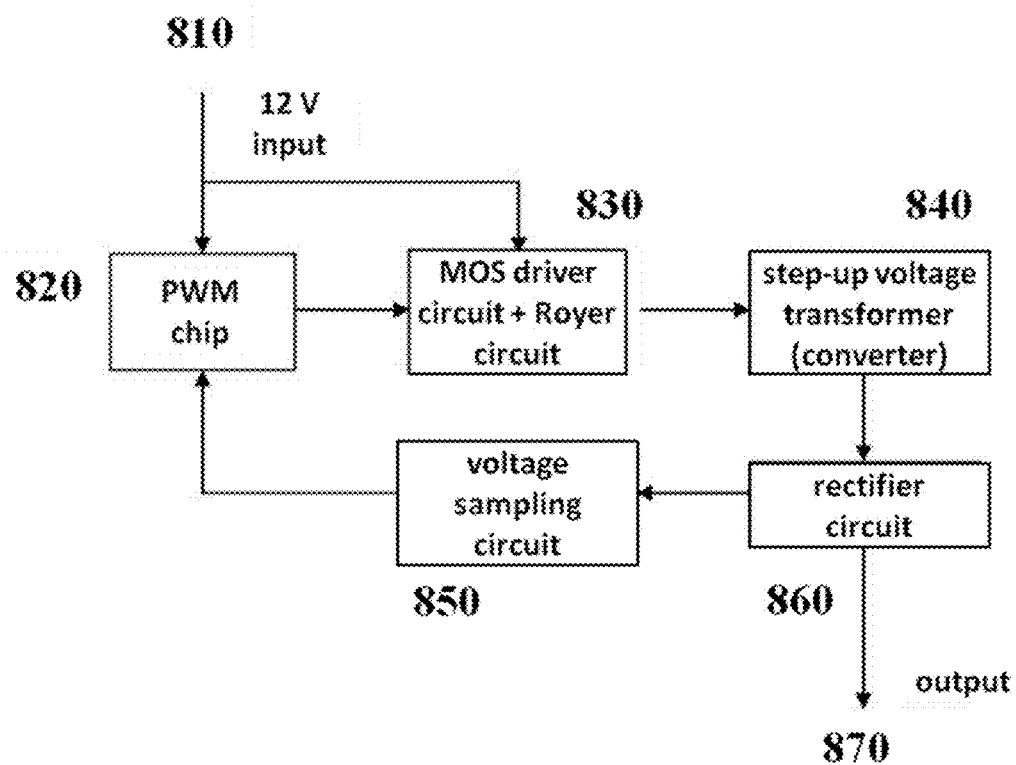
FIG. 8 shows an exemplary schematic of a high voltage circuit.

The high voltage power supply circuit can comprise the circuit shown in FIG. 8. An input voltage signal (e.g., a 12 V input) 810 can be fed to a pulse width modulation (PWM) chip 820 and a MOS driver circuit with Royer circuit 830. The PWM chip can also drive the MOS driver circuit with Royer circuit. Output from the MOS driver circuit with Royer circuit can be fed into a step-up voltage transformer or converter 840. The stepped-up voltage signal can be rectified with a rectifier circuit 860 (e.g., a full-bridge rectification circuit) to produce a high voltage DC output 870. Signal from the rectifier circuit can also be sampled with a voltage sampling circuit 850 and used in a closed-loop voltage regulator circuit to produce a constant voltage output.

Figure 9:
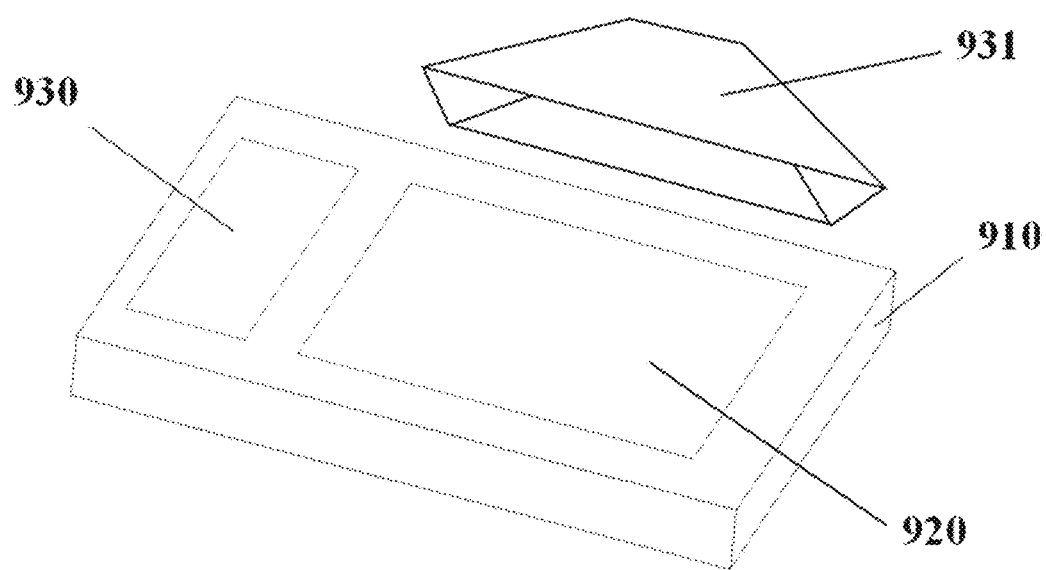
FIG. 9 shows an exemplary schematic of an electrophoresis apparatus with an illuminating area, voltage control and display, and imaging equipment.

Imaging or detection equipment can be used in conjunction with electrophoresis apparatuses. An electrophoresis apparatus 910 can comprise an illuminating area 920 and a voltage control and display area 930, as shown for example in FIG. 9. Imaging equipment 931 can comprise elements including but not limited to a camera, a separate power supply, and communication equipment. The communication equipment can comprise wireless communication equipment (e.g., Wi-Fi, Bluetooth) and/or wired communication equipment (e.g., USB). The camera can comprise a big aperture, which can decrease imaging height. The camera can comprise a wide-angle lens. The imaging equipment can utilize filters or other image processing techniques, including quadratic filters, Kalman filters, and distortion correction (e.g., fisheye correction).

The apparatus can comprise a light source. The light source can be integrated into the detector housing or the electrophoresis apparatus housing. The light source can comprise a lamp, such as an incandescent, halogen, fluorescent, gas-discharge, arc, laser, UV, or LED lamp. The light source can comprise a laser. The light source can produce a specific wavelength or range or wavelengths, including but not limited to visible light, infrared light, UV light, and combinations thereof. The light source can comprise multiple light sources, of the same or of different types, which can be used separately or in combination.

Figure 10:
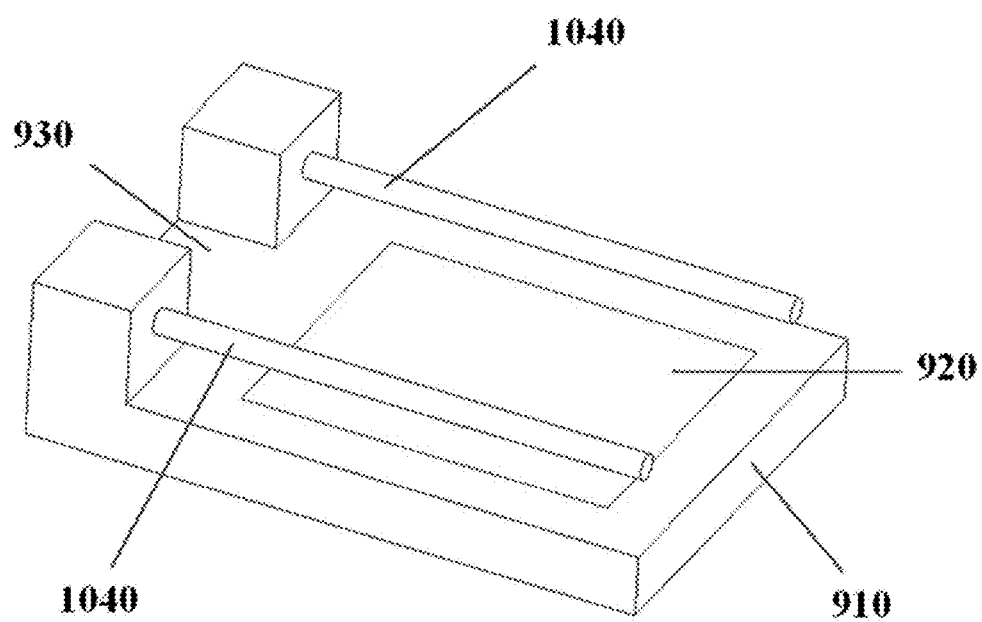
FIG. 10 shows an exemplary schematic of an electrophoresis apparatus with electrodes.
Figure 11:
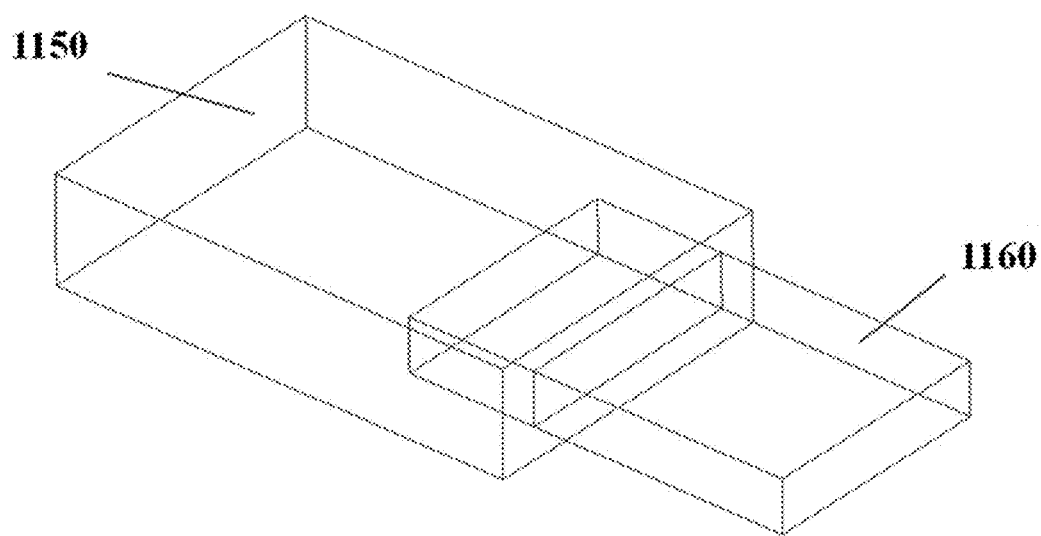
FIG. 11 shows an exemplary schematic of a drawer-like electrophoresis apparatus with a moveable gel tray.
Figure 12:
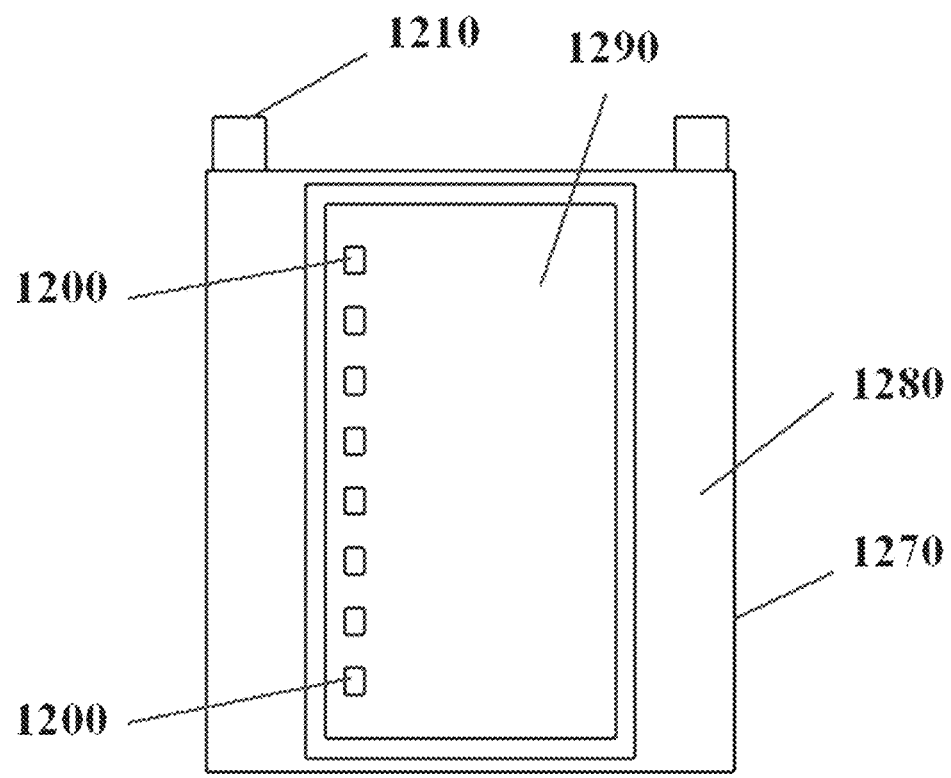
FIG. 12 shows an exemplary schematic of a gel tray with a buffer trough, gel region, sample wells, and electrodes.
Figure 13:
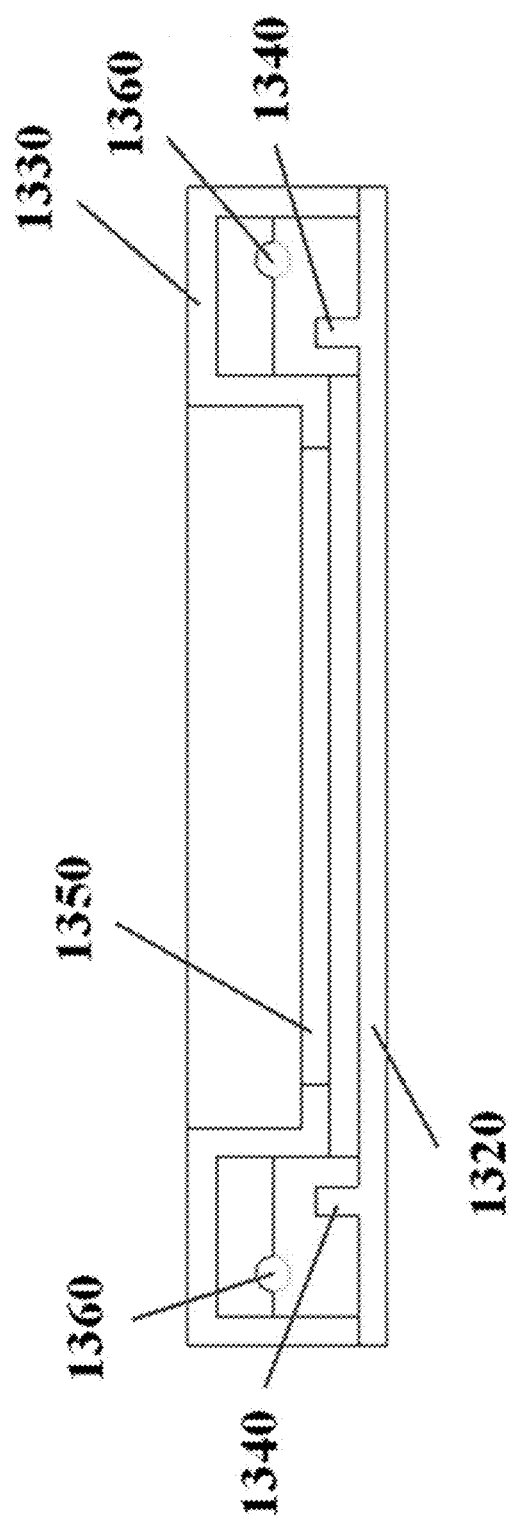
FIG. 13 shows an exemplary cross-section schematic of a gel tray.

In some cases, electrodes 1040 can be separated from the electrophoresis apparatus 910 or its gel tray, for example as shown in FIG. 10. The electrophoresis apparatus can comprise a drawer-like structure 1150 with a moveable gel tray 1160, for example as shown in FIG. 11. The drawer can be movable manually or automatically. The gel tray 1270 can comprise elements including a buffer trough or chamber 1280, a gel region 1290, sample wells 1200, and electrodes 1210, for example as shown in FIG. 12. A cross-section of a gel tray is shown for example in FIG. 13, with a lower gel tray panel 1320, an upper gel tray panel 1330, a buffer stopper or weir 1340, a gel region upper panel 1350, and electrodes 1360.

Figure 14:
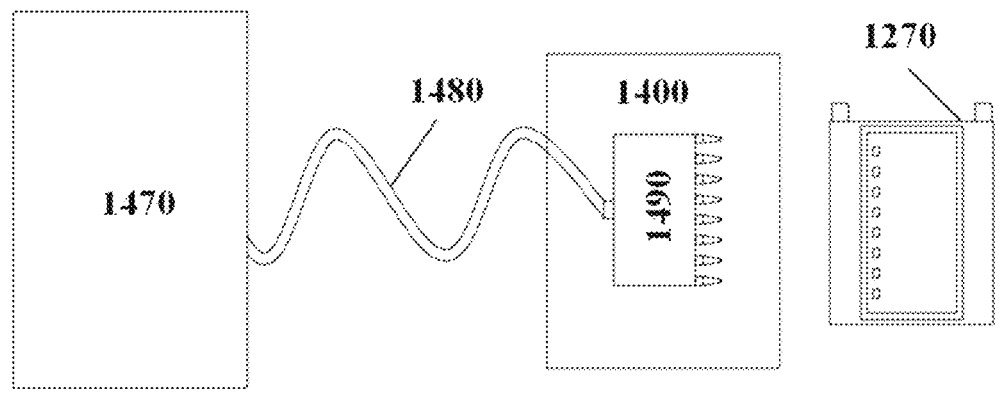
FIG. 14 shows an exemplary schematic of a gel casting system.
Figure 15:
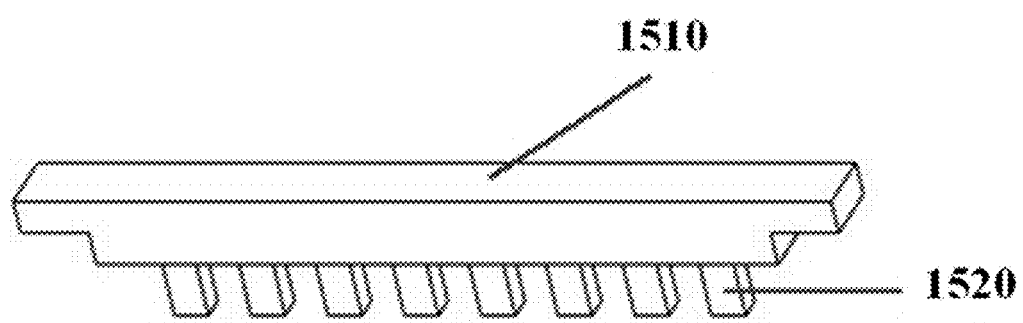
FIG. 15 shows an exemplary schematic of a comb.
Figure 16:
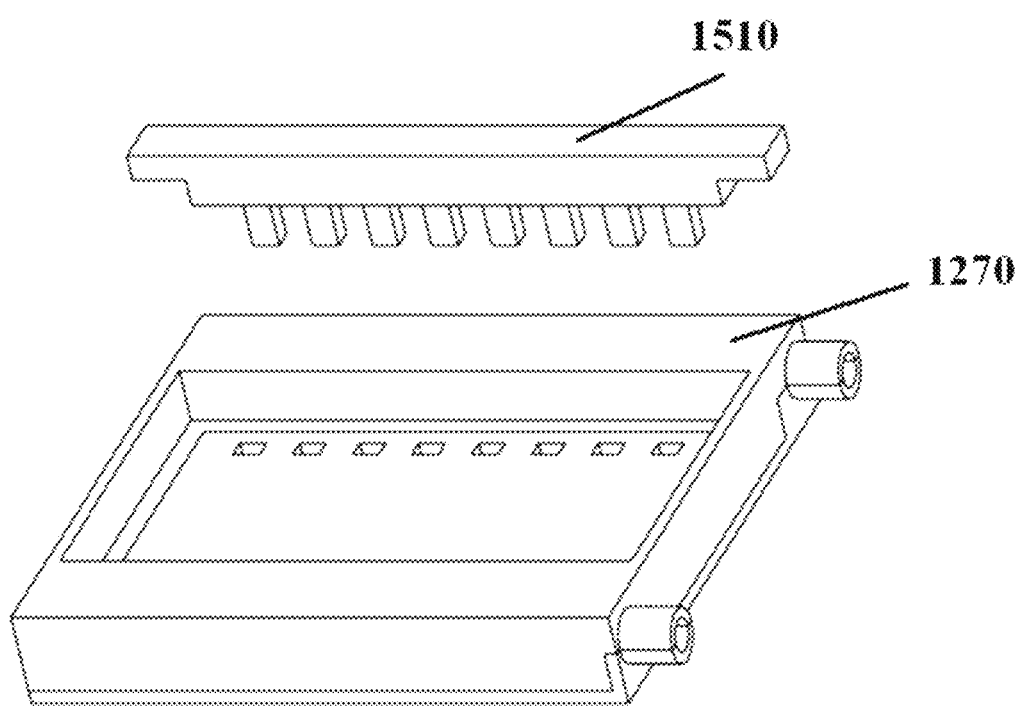
FIG. 16 shows an exemplary schematic of a comb and a gel tray.

Gel can be cast using a gel casting system. Gel casting systems can comprise components including a pump 1470, a pipe, tube, or other conduit 1480, a gel injector (e.g., auto pipette) 1490, and a heating zone 1400, for example as shown in FIG. 14. FIG. 15 and FIG. 16 show a comb 1510 with teeth 1520 which can be used to form wells in a gel.

The electrophoresis apparatus can have a housing that covers and/or encloses one or more components of the electrophoresis apparatus. The housing can comprise different shapes and form factors, as shown in FIG. 17-23 and FIG. 27-29. Imaging or detecting equipment 1720 can be located in a separate housing from the electrophoresis apparatus 1710 (e.g., FIG. 17), and can be configured to mount onto the electrophoresis apparatus for imaging (e.g., FIG. 18). Such mounting can reduce or eliminate the exposure of the gel to outside light. The electrophoresis apparatus housing can comprise a sliding gel tray 1930 as previously described (e.g., FIG. 19). The mounting of the imaging or detecting equipment can utilize a variety of methods or motions 2040 (e.g., FIG. 20). Mounting can be aided by connectors, tabs, or other adaptors 2150 on the apparatus housing (e.g., FIG. 21). The imaging or detector equipment housing can comprise different shapes and form factors (e.g., FIG. 22). The form factor of the electrophoresis housing can be small (e.g., FIG. 23). The housing can comprise a front slide panel 2710, which can be opened 2730 to allow loading or unloading of an electrophoresis matrix 2740, as well as a top slide panel which can be opened to allow access to an observation window 2720 for viewing an electrophoresis matrix loaded in the apparatus (e.g. FIG. 27). The housing 2810 can comprise a front slide panel 2811 and a top slide panel 2812, as well as a main switch 2821, power supply cable 2822, light tuning control 2823, and light source switch 2824 (e.g. FIG. 28A, FIG. 28B, FIG. 28C). The front slide panel can be opened or closed by sliding (e.g., FIG. 28D). An electrophoresis matrix 2830 can be loaded or unloaded via the front slide panel (e.g., FIG. 28E). The housing can comprise a control interface 2840, such as a touch control interface, which can be used to manually control voltage or other operational parameters (e.g., FIG. 28F). In some cases, the control interface can be visible only when the device is operating. The housing can comprise a top slide panel 2850, which can be opened to allow access to an observation window 2851 (e.g., FIG. 28G, FIG. 28H).

Some or all of the components necessary for conducting electrophoresis can be integrated within the electrophoresis apparatus housing. For example, the gel tray and power supply can both be integrated into the same housing. A light source for imaging or detection can be integrated within the apparatus housing. Communications equipment, such as wireless (e.g., Wi-Fi, Bluetooth) or wired (e.g., USB) communication equipment, can be integrated within the housing.

Figure 24:
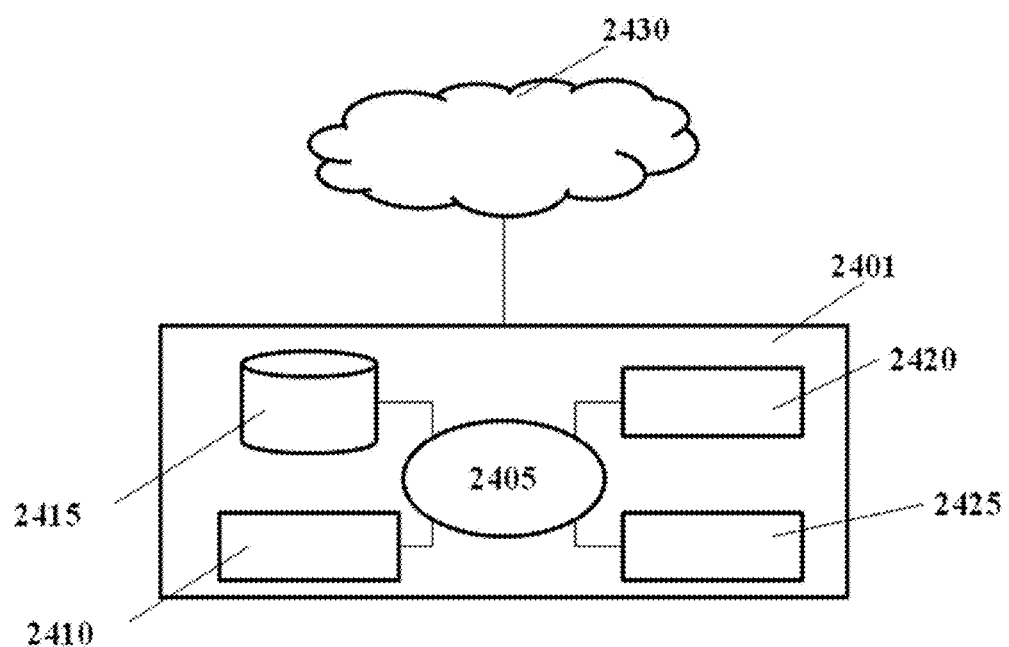
FIG. 24 shows an exemplary computer system for performing electrophoresis.
Figure 25:
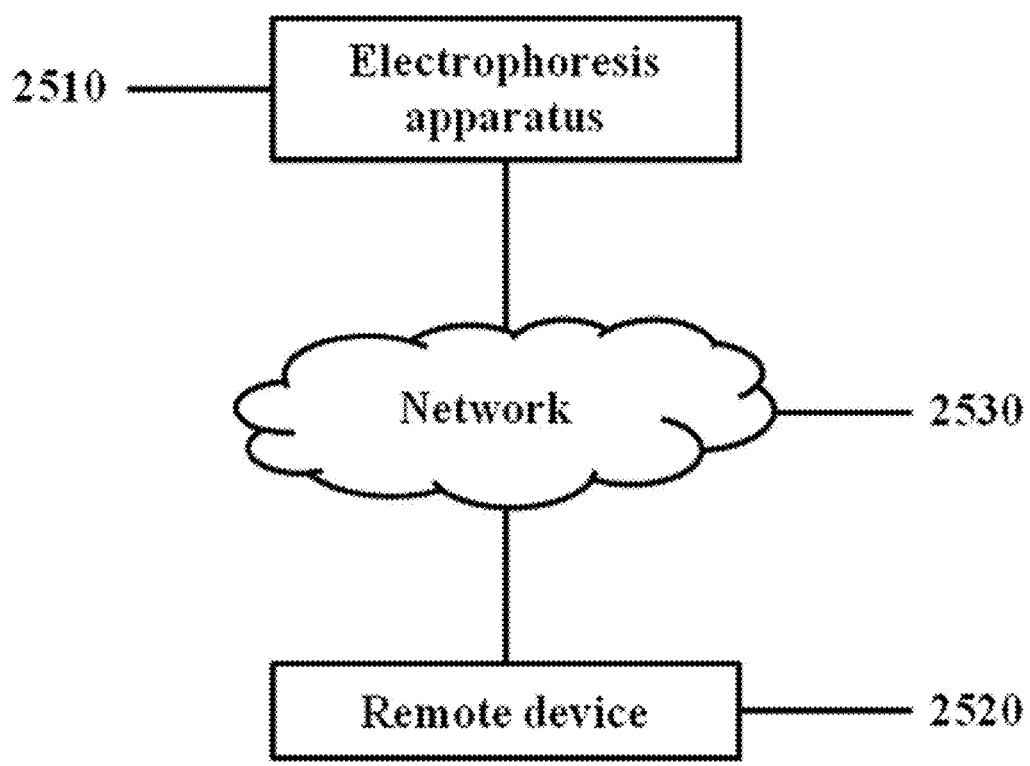
FIG. 25 shows an exemplary electrophoresis apparatus communicating with a remote device over a network.
Figure 26:
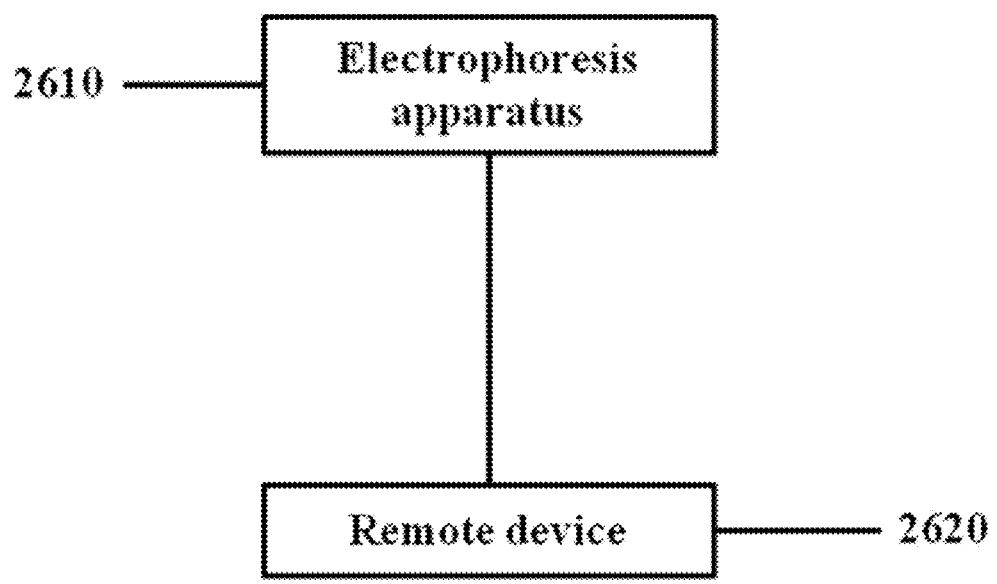
FIG. 26 shows an exemplary electrophoresis apparatus communicating with a remote device directly.

Control systems can be used in combination with the electrophoresis apparatus and associated equipment. For example, FIG. 24 shows a computer system 2401 that is programmed or otherwise configured to perform electrophoresis. FIG. 25 and FIG. 26 show schematics of an electrophoresis apparatus 2510, 2610 communicating with a remote device 2520, 2620, either over a network 2530 (FIG. 25) or directly (FIG. 26).

Figure 29:
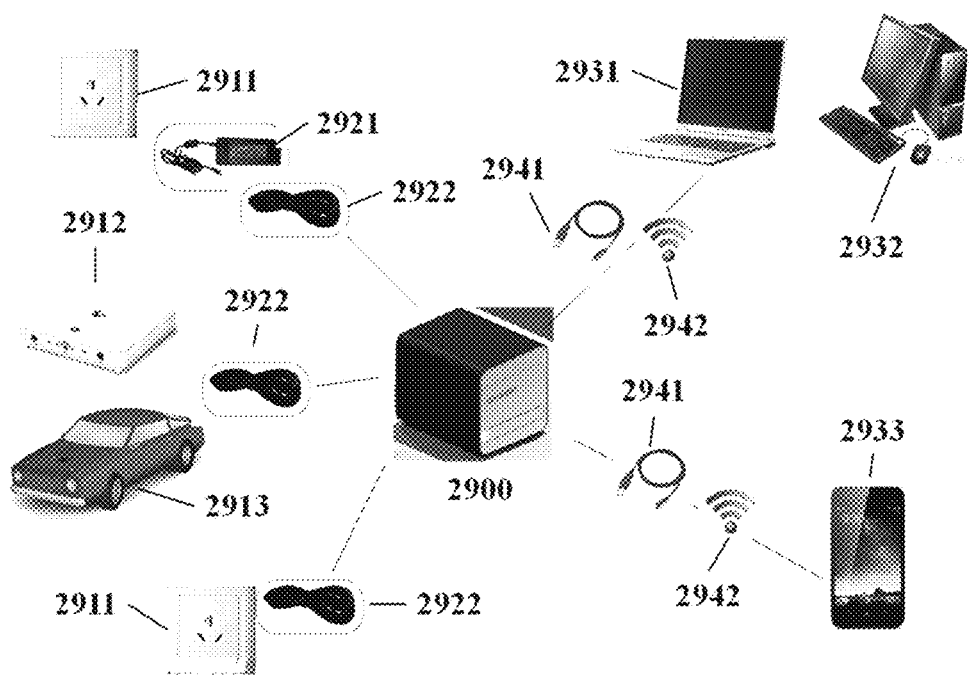
FIG. 29 shows an exemplary diagram of connection options for connecting an electrophoresis apparatus to a power source or a computer.

The electrophoresis apparatus 2900 can connect with power sources such as wall outlets 2911, battery packs 2912, or motor vehicle power systems 2913, either through an adaptor 2921 and a power cable 2922, or directly through a power cable 2922 (e.g., FIG. 29). The apparatus can connect with computer systems such as laptop computers 2931, desktop computers 2932, or mobile devices 2933, either through a cable 2941 or wirelessly 2942 (e.g., FIG. 29).

Power Supply

The electrophoresis apparatus can comprise a power supply. The power supply can be external to the apparatus housing or integrated within the apparatus housing. The power supply can comprise adaptors for connection to external power sources. External power sources can include, but are not limited to: residential, commercial, or industrial building power, 12 V DC sources, off-grid sources, renewable energy sources, solar panels, batteries or other energy storage devices, motor vehicles, and motor vehicle batteries.

The power supply may include one or more batteries of the electrophoresis apparatus. Any description of any power supply may apply to the batteries or vice versa. Any description of a battery or batteries may apply to a battery pack and vice versa. A battery pack may include one or more batteries. Multiple batteries may be connected to one another in series, in parallel, or any combination thereof.

The power supply can be configured to run on a low voltage input signal. The low voltage input can provide a voltage of at most about 64 V, 50 V, 48 V, 36 V, 30 V, 29 V, 28 V, 27 V, 26 V, 25 V, 24 V, 23 V, 22 V, 21 V, 20 V, 19 V, 18 V, 17 V, 16 V, 15 V, 14 V, 13 V, 12 V, 11 V, 10 V, 9 V, 8 V, 7 V, 6 V, 5 V, 4 V, 3 V, 2 V, or 1 V DC. In some embodiments, the low voltage input may be greater than one or more values of described herein, or may fall in a range between any two of the values described herein. In some cases, the low voltage input can provide at most about 14.5 V DC. In some cases, the low voltage input can provide at most about 12.5 V DC. The power supply may optionally provide a voltage of no more than about 24 V or 12 V to the electrophoresis apparatus.

The power supply can provide an output voltage to the electrodes, resulting in a field strength or voltage gradient needed for electrophoresis. The output voltage can be about 1 V, 2 V, 3 V, 4 V, 5 V, 6 V, 7 V, 8 V, 9 V, 10 V, 15 V, 20 V, 25 V, 30 V, 35 V, 40 V, 45 V, 50 V, 60 V, 70 V, 80 V, 90 V, 100 V, 200 V, 300 V, 400 V, 500 V, 600 V, 700 V, 800 V, 900 V, 1 kV, 2 kV, 3 kV, 4 kV, 5 kV, 6 kV, 7 kV, 8 kV, 9 kV, 10 kV, 15 kV, 20 kV, 25 kV, 30 kV, 35 kV, 40 kV, 45 kV, 50 kV, 60 kV, 70 kV, 80 kV, 90 kV, or 100 kV. The output voltage can be at least about 1 V, 2 V, 3 V, 4 V, 5 V, 6 V, 7 V, 8 V, 9 V, 10 V, 15 V, 20 V, 25 V, 30 V, 35 V, 40 V, 45 V, 50 V, 60 V, 70 V, 80 V, 90 V, 100 V, 200 V, 300 V, 400 V, 500 V, 600 V, 700 V, 800 V, 900 V, 1 kV, 2 kV, 3 kV, 4 kV, 5 kV, 6 kV, 7 kV, 8 kV, 9 kV, 10 kV, 15 kV, 20 kV, 25 kV, 30 kV, 35 kV, 40 kV, 45 kV, 50 kV, 60 kV, 70 kV, 80 kV, 90 kV, or 100 kV. The output voltage can be at most about 1 V, 2 V, 3 V, 4 V, 5 V, 6 V, 7 V, 8 V, 9 V, 10 V, 15 V, 20 V, 25 V, 30 V, 35 V, 40 V, 45 V, 50 V, 60 V, 70 V, 80 V, 90 V, 100 V, 200 V, 300 V, 400 V, 500 V, 600 V, 700 V, 800 V, 900 V, 1 kV, 2 kV, 3 kV, 4 kV, 5 kV, 6 kV, 7 kV, 8 kV, 9 kV, 10 kV, 15 kV, 20 kV, 25 kV, 30 kV, 35 kV, 40 kV, 45 kV, 50 kV, 60 kV, 70 kV, 80 kV, 90 kV, or 100 kV. The field strength can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 48 V/cm. The field strength can be at least about 1, 2, 3, 4, 5, 6, 7, 8, 9, 10, 11, 12, 13,14, 15, 16, 17, 18, 19, 20, 21, 22, 23, 24, 25, 26, 27, 28, 29, 30, 31, 32, 33, 34, 35, 36, 37, 38, 39, 40, or 48 V/cm. The field strength can be about 1, 2, 3, 4, 5, 6, 7, 8, 9, 10, 11, 12, 13,14, 15, 16, 17, 18, 19, 20, 21, 22, 23, 24, 25, 26, 27, 28, 29, 30, 31, 32, 33, 34, 35, 36, 37, 38, 39, 40, or 48 V/cm. In some cases, the field strength can be between about 1 and about 2 V/cm. In some cases, the field strength can be between about 4 and about 10 V/cm. In some cases, the field strength can be between about 5 and about 8 V/cm. In some cases, the field strength can be between about 5 and about 10 V/cm. In some cases, the field strength can be between about 10 and about 20 V/cm.

The field strength can be adjustable. The field strength can vary during the course of an electrophoresis. Different electrophoresis techniques can be implemented within the electrophoresis apparatus, including but not limited to, gel electrophoresis, pulsed field gel electrophoresis, isoelectric focusing, mobility shift electrophoresis, affinity electrophoresis, and isotachophoresis.

The power supply can be compatible with a car power adaptor or cigarette lighter adaptor. The sockets and plugs used for connection with a car power adaptor can be those defined in the ANSI/SAE J563 specification. In some cases, the adaptor socket and plug can be size A, with the receptacle having an inside diameter of about 20.93 mm to about 21.01 mm and the plug body having a diameter of about 20.73 mm to about 20.88 mm. In some cases, the adaptor socket and plug can be size B, with the receptacle having an inside diameter of about 21.41 mm to about 21.51 mm and the plug body having a diameter of about 21.13 mm to about 21.33 mm. The plug can include a light to indicate a connection has been made. The power supply can be capable of drawing power from a cigarette lighter adaptor or other charging port of a motor vehicle. The power supply can draw power while the motor vehicle is running or not running. The power supply can draw power while the motor vehicle is in motion or is not in motion.

The power supply can comprise various circuit elements, such as control elements, drivers, transformers, rectifiers, and sampling elements. The power supply can be capable of providing high voltage. The power supply can comprise pulse width modulation circuits or chips. The power supply can comprise drivers, such as MOS drivers. The power supply can comprise oscillators, such as Royer circuits. The power supply can comprise transformers, such as step-up voltage transformers. The power supply can comprise rectifiers, such as full-bridge rectifier circuits. The power supply can comprise sampling circuits, such as voltage sampling circuits. The power supply can comprise controls or regulators, such as a closed-loop voltage regulator circuit. The power supply can produce a constant or about constant high voltage output. The electrophoresis apparatus can comprise a voltage display circuit 710, which can display voltage information from a high voltage power supply circuit 720, as shown in FIG. 7. Apparatuses can also comprise light control circuits 730. Circuits can be used in the control of an integrated apparatus or system 740, comprising a high voltage source 750, a display 760, and a light source 770 in one integrated system.

For example, the high voltage power supply circuit can comprise the circuit shown in FIG. 8. An input voltage signal (e.g., a low voltage input such as a 12 V input) 810 can be fed to a pulse width modulation (PWM) chip 820 and a MOS driver circuit with Royer circuit 830. Input voltage signals can comprise a low voltage signal, such as any low voltage signal described elsewhere in this disclosure. The PWM chip can also drive the MOS driver circuit with Royer circuit. Output from the MOS driver circuit with Royer circuit can be fed into a step-up voltage transformer or converter 840. The stepped-up voltage signal can be rectified with a rectifier circuit 860 (e.g., a full-bridge rectification circuit) to produce a high voltage DC output 870. Signal from the rectifier circuit can also be sampled with a voltage sampling circuit 850 and used in a closed-loop voltage regulator circuit to produce a constant voltage output.

Various components of the electrophoresis apparatus can run from the low voltage input, such as 24 V or 12 V or other low voltage values described elsewhere herein. In some cases, the high voltage source for the electrodes can run from the low voltage input. In some cases, the high voltage source for the electrodes and the voltage control and display circuits can run from the low voltage input. In some cases, the integrated apparatus or system, comprising a high voltage source, a display, and a light source in one integrated system can run from the low voltage input. In some cases, the high voltage source for the electrodes, the control and display circuits, the light source, and the communication equipment can run from the low voltage input. In some cases, the high voltage source for the electrodes, the control and display circuits, the light source, the communication equipment, and the detector can run from the low voltage input.

An electrophoresis apparatus may be capable of performing electrophoresis when running on a low voltage, such as a voltage less than about 24 V or 12 V or other low voltage values described elsewhere herein. The electrophoresis apparatus may be capable of powering one or more electrodes to cause the sample to migrate through the gel. Sample may be capable of migrating through the gel as the electrophoresis apparatus receives a low voltage. In some instances, a low voltage, such as a voltage less than about 24 V or 12 V or any other low voltage values described elsewhere herein, may be used to perform the combination of electrophoresis and detecting. The electrophoresis apparatus may be capable of powering one or more electrodes to cause the sample to migrate through the gel while powering a detector that detects the progress of the sample migration in real-time. Sample may be capable of migrating through the gel, and the detector may be capable of detecting the sample progress in real-time, as the electrophoresis apparatus receives a low voltage. Optionally, the low voltage may also power a light source of the electrophoresis. The electrodes, the electrodes and detector, the electrodes and detector and light source, the detector and light source, the electrodes and light source, or any combination thereof may be powered by using a low voltage value. Thus, real-time electrophoresis may occur, powered by a low voltage.

The low voltage may be powered from a low voltage external power source. For example, the electrophoresis application may be powered by a motor vehicle, an off-grid power source, an energy storage device, or any other external power source as described elsewhere herein.

The overall power consumption of the electrophoresis apparatus can be low. In some cases, the overall power consumption of the electrophoresis apparatus is less than or equal to about 12 W. In some instances, a low degree of power may be used for electrophoresis, or the combination of electrophoresis and detection. For instance, about 100 W may be used to perform the electrophoresis and detecting. In some instances, a low power may be less than or equal to about 250 W, 200 W, 150 W, 130 W, 120 W, 110 W, 100 W, 90 W, 85 W, 84 W, 83 W, 80 W, 75 W, 70 W, 65 W, 60 W, 55 W, 50 W, 45 W, 40 W, 35 W, 30 W, 25 W, 20 W, 15 W, 14 W, 13 W, 12 W, 11 W, 10 W, 9 W, 8 W, 7 W, 6W, 5 W, 4 W, 3 W, 2 W, 1 W, 500 mW, 100 mW, 50 mW, 10 mW, 5 mW, or 1 mW. In some cases, a low power may be from about The amount of power used to operate the device may be less than or equal to any of the values described herein. Alternatively, the amount of power used to operate the device may be greater than equal to any of the values described herein. The amount of power used to operate the device may fall into a range between any two of the values described herein. The amount of power used to operate the electrophoresis apparatus (e.g., electrodes) and detector may have a total less than any of the values described herein. The amount of power used to operate the electrophoresis apparatus and detector may have a total greater than any of the values described herein. The amount of power used to operate the electrophoresis apparatus and detector may fall into a range between any two of the values described herein.

An electrophoresis apparatus may receive power via a single power cable. In some cases, a single power cable provides power for electrophoresis operation In some cases, a single power cable provides power for electrophoresis operation and a light source. In some cases, a single power cable provides power for electrophoresis operation and a detector. In some cases, a single power cable provides power for electrophoresis operation, and a light source, and a detector. In some cases, a single power cable provides power for all the elements enclosed in the electrophoresis apparatus housing. An electrophoresis apparatus may receive power via two power cables. In some cases, a two power cables provide power for electrophoresis operation In some cases, two power cables provide power for electrophoresis operation and a light source. In some cases, two power cables provide power for electrophoresis operation and a detector. In some cases two power cables provide power for electrophoresis operation, and a light source, and a detector. In some cases, two power cables provide power for all the elements enclosed in the electrophoresis apparatus housing. In some cases, power for a light source is provided via a separate power cable. The electrophoresis apparatus can connect with power sources such as wall outlets 2911, battery packs 2912, or motor vehicle power systems 2913, either through an adaptor 2921 and a power cable 2922, or directly through a power cable 2922 (e.g., FIG. 29).

An electrophoresis apparatus may be powered by a vehicle in accordance with an embodiment of the invention. A device may be electrically connected to a charging port of a vehicle. Electrical energy may flow from the charging port to the device. The vehicle may be a self-propelled vehicle having one or more propulsion unit.

The device may be a portable device capable of conducing electrophoresis. The device may be useful for real-time electrophoresis. The device may be capable of operating using low voltage of power. The device may be capable of operating using less than 12 V of power, or any other voltage of power described elsewhere herein. The device may be capable of fitting within a vehicle. The device may be capable of fitting onto a seat of a vehicle. The device may be capable of resting on a lap of an individual sitting within a vehicle.

The vehicle may be a passenger vehicle. The vehicle may be sedan, hatchback, station wagon, truck, SUV, mini-van, van, jeep, tank, unmanned vehicle, or any other type of automotive vehicle capable of self-propulsion. In some instances, the vehicle may be an airplane, helicopter, train, monorail, subway, boat, ship, or any other type of vehicle. The vehicle may be propelled with aid of an internal combustion engine. The vehicle may be propelled with aid of an electric motor. The vehicle may have a vehicle battery that may power one or more component of the vehicle. The vehicle may be capable of fitting about two, three, four, five, six or more people therein. The vehicle may include one or more propulsion units, such as wheels that may permit the vehicle to move in an environment.

The vehicle may have a charging port thereon. The charging port may be in an interior of the vehicle. The charging port may be may be a cigarette lighter receptacle for an automobile. The charging port may be a DC power source. The charging port may be a 12 V receptacle. The charging port may include a socket configured to receive a charging connector. The charging port may be a 12 V auxiliary power outlet of the vehicle. In some instances, the charging port may be a 5 V outlet. The charging port may be a USB standard 5 V outlet. The charging port may provide any low voltage value, such as those described elsewhere herein. The charging port may be provided in accordance with ANSI/SAE J563 specifications, as described elsewhere herein.

The charging port may provide power that may originate from a battery of a vehicle. A device electrically connected to a charging port may be powered by a battery of a vehicle. The battery of a vehicle may be a car battery or any type of automotive battery. The vehicle battery may be a starting, lighting, ignition (SLI) battery. The vehicle battery may be a lead-acid battery. Optionally, the vehicle battery may include six galvanic cells that may deliver a total of about 12 V or less. In some instances, a vehicle may have multiple automotive batteries that may deliver a total of about 24 V or less. In some instances, a vehicle may have one or more automotive batteries that may deliver a total of about 48 V or less.

When a power connector of the electrophoresis device is connected to the charging port, power may flow from the charging port of the vehicle to the device. The power may flow when the vehicle is operational. The vehicle may or may not be in motion while the vehicle is in operation. The vehicle may be operational when it is powered on and/or the engine is running. The vehicle may be in operation when the vehicle's ignition is not completely turned off. The vehicle may be in operation when one or more wheels of the vehicle are turning. The vehicle may be in operation when the vehicle is in parking mode with the ignition on. The vehicle may be in operation if the vehicle headlights or radio may be turned on. Power may or may not flow to the device when the vehicle is not in operation.

The power may be used to directly operate the device. The power may be used to charge an energy storage unit. The energy storage unit may be used to operate the device. In some instances, one or more set of protocols may be used to govern whether the power flowing to the device is used to directly operate the device or charge an energy storage device that may be used to power the device. In some instances, both actions may simultaneously occur.

The device may be connected to a charging port via a power connector. The power connector may include a plug that may fit into the charging port. The device may come equipped with a power connector that may be configured to directly connect to the charging port. The power connector may include one or more prongs, pins, indentations, or conductive surfaces.

The charging port may be capable of providing low voltage power to the device to permit operation of the electrophoresis device. The charging port may be on-board the vehicle. The charging port may be any off-grid charging port. The charging port may be powered by a vehicle battery.

The charging port may be any other type of charging port electrically connected to any type of external power source as described elsewhere herein.

Alternatively, the electrophoresis device may be connected to a charging port via a power connector and an adaptor. The power connector may not directly fit into the charging port, or may not be configured to regulate the power coming from the charging port for operation of the vehicle. The adaptor may provide one or more of these functions. The adaptor may be provided between the power connector of the device and the charging port.

The adaptor may be configured to physically fit into the charging port. The adaptor may be configured to mechanically and/or electrically connect to the charging port. The power connector may be not be capable of directly mechanically and/or electrically connecting to the charging port. In some instances, the adaptor may or may not provide some power regulation or conversion when providing power to the power connector. For example, the adaptor may convert DC to AC. In another example, the adaptor may modify or regulate voltage and/or current from the charging port to the power connector.

Any description herein of connecting the device to the charging port may or may not include the use of one or more adaptors.

An electrophoresis device may be deployed with aid of one or more vehicles. The device may be a portable device that can be carried within a vehicle. The vehicle may provide power to the device at a low voltage power, such as 12 V or other voltage values described elsewhere herein. The power provided to the device may be used to charge an energy storage unit of the device and/or directly power one or more other component of the device. The power may be provided to the device via a charging port while the vehicle is turned on. The power may be provided to the device while the vehicle is stationary or while the vehicle is in motion. The device may thus advantageously be deployed to multiple locations. These may include remote locations that may otherwise not have the power sources capable of powering the device. These may include remote locations where rolling blackouts may occur so reliable access to power may not be provided.

The electrophoresis device may receive a sample at a location. The device may conduct electrophoresis at the location or while the device is in transit to another location. The device may receive the sample while the device is outside the vehicle, or may receive the sample while the device is within the vehicle. The device may receive the sample while the vehicle is stationary or in motion.

The device may be connected to a charging port of the vehicle while it is in operation. Alternatively, the device may be disconnected from a charging port of the vehicle while it is in operation. The device may have an energy storage unit that may store energy while the device is connected to the vehicle. When the device is disconnected from the vehicle, the energy storage unit may be used to power the device. This may permit the device to be charged while in transit to a location. The device may then be taken out of the vehicle and used to conduct electrophoresis at the location using the stored energy. If the device depletes the charge of the energy storage unit, the device may be re-connected to the vehicle to power the device and/or charge the energy storage unit. Thus, as long as a vehicle is available, a ready power source may be provided for the device. This may advantageously couple transport of a device to a remote location with powering the device at any location to which it has been transported.

Any description herein of a vehicle may also apply to any other type of power source, such as those described elsewhere herein.

One or more different locations may be provided. The locations may or may not be remote from one another. Infrastructure such as roads (or paved roads) may or may not exist between the various locations.

In some instances, samples may be provided from subjects that are in the proximity of the device. For example, samples from subjects at or near a first location may be provided. In other instances, samples may be provided from subjects that are at other locations. The remote samples may be sent from the other locations to a facility. In some instances, this may delay results getting back to the subjects or individuals at the other locations.

A vehicle may be sent to another location (e.g., a second location). The vehicle may have a device for conducting electrophoresis. The device may optionally be electrically connected to the vehicle while the vehicle is in operation. The device may be powered and/or charged by the vehicle when the vehicle is in operation. The device may be powered and/or charged by the vehicle while the vehicle is in motion (e.g., from a first location to a second location). Permitting a device to be charged while the vehicle is in transit may permit the device to be at a substantially charged state when the device arrives at the destination. In some instances, the device may be used at the destination to perform electrophoresis at the location. The device may be powered by the vehicle at the location. For example, a car or other type of vehicle may be turned on and used to power a device while the device is running the electrophoresis at the location. Alternatively, the device may operate at the location using an energy storage device that has already been charged. The energy storage device may have been charged while the device was in transit. Charging the device while the device is in transit may advantageously provide greater flexibility that may allow the vehicle or apparatus to be transported from one location to another. The locations need not have grid power sources, or the use of the device need not rely on grid power sources. Furthermore, the device may be charged to a ready-to-use state while in transit which may save time when the device arrives at a destination.

In some instances, one or more subjects may provide a sample at a destination. The electrophoresis may occur at the destination. Point of care (POC) testing may permit the results to be provided at the destination. In some instances, real-time electrophoresis or detection may occur, which may permit results to be provided in real-time or instantaneously to subjects at the location. This may permit the nucleic acid amplification device to be brought to otherwise remote locations and allow testing that may provide much faster results than other situations. This may be advantageous for disease prognosis and/or treatment. This may also aid in the detection and prevention of spreading infectious diseases.

In some instances, the testing may occur at the destination location. In some instances, the samples may be collected and/or loaded into the device at the destination location. The device may be used to perform electrophoresis on the sample at the destination location. The results may be delivered at the destination location. In other implementations, a vehicle may receive the device and depart the destination location. The vehicle may be on its way to another location, such as a lab or facility. The device may be capable of performing electrophoresis in the vehicle while the vehicle is in operation. The device may be capable of performing electrophoresis while the vehicle is in transit. The device may be powered by the vehicle to perform the electrophoresis. In some instances, after the samples have been loaded into the device at a location, the vehicle may make its way to another location. The amplification may occur and/or be completed while the vehicle is in transit. This may save time in getting the device to another location where it may be needed. The results may be detected with aid of an on-board detector. The results may be relayed to a user of the device in real-time. The results may be relayed back to the location from which the samples were collected. In some instances, the results may be relayed to a facility which may perform additional analysis.

Powering the device using the vehicle, and permitting nucleic acid amplification and detection while the device is in the vehicle en route may provide greater flexibility and time saving measures. The vehicle transit time may be used, rather than being 'down time.' This may aid in maximizing or improving the use of the device when the device is deployed to different locations.

Electrophoresis Gel and Lanes

The electrophoresis apparatus can comprise an electrophoresis matrix (e.g., a gel). The matrix can be divided into lanes separated by solid barriers. For example, FIG. 1 and FIG. 2A show a schematic of an electrophoresis matrix 110, from three-quarters and top-down views, respectively. The electrophoresis matrix can comprise gel lanes 120. Physical barriers 125 can provide physical separation between samples running in neighboring gel lanes or channels. The electrophoresis matrix can comprise troughs or chambers 130 for holding buffer or other fluids. The electrophoresis matrix can comprise electrodes 140. FIG. 3 shows a side-view schematic of a gel lane, with electrodes 350 positioned on the ends, and with buffer 360 positioned in buffer chambers between the electrodes and the gel 370.

Gel or matrix lanes, defined by solid barriers, can be open on top rather than enclosed. For example, the gel lanes may optionally not be covered. The gel lanes may have sides enclosed by the solid barriers while the top is open and does not contact a solid barrier. That is, gel lanes can be partially or totally physically separated side-to-side while sharing a common overhead space, whereby a fluid (e.g., buffer, air) can be in contact or communication with some or all of the lanes. For instance, a top surface of a gel in a first lane may be in fluid communication with a top surface of a gel of a second lane. A shared overhead space may span all the lanes in the electrophoresis matrix. Alternatively, the shared overhead space may span a subset of the lanes in the electrophoresis matrix. In some embodiments, a top surface of the gel in the lanes may be visually discernible from over the electrophoresis matrix. Gel or matrix lanes can comprise capillary channels, capillary tubes, capillary gels, or microfluidic channels. Barriers can extend completely or partially into the depth of the gel or matrix. Barriers can extend at least about 10%, 20%, 30%, 40%, 50%, 60%, 70%, 80%, 90%, or 100% through the thickness of the gel or matrix. Barriers can extend the entire length or part of the length of the gel or matrix lane. Barriers can extend at least about 10%, 20%, 30%, 40%, 50%, 60%, 70%, 80%, 90%, or 100% of the length of the gel or matrix lane. Barriers can prevent, reduce, or inhibit diffusion or other transport of material (e.g., sample material) between adjacent lanes. Barriers can reduce or inhibit transport of material between adjacent lanes by at least about 10%, 20%, 30%, 40%, 50%, 60%, 70%, 80%, 90%, or 100% compared to a gel without barriers.

Barriers can comprise one or more connectors between gel lanes. For example, FIG. 2B and FIG. 2C show connectors 260 allowing transport of material between gel lanes. Such transport can be facilitated by additional electrodes oriented to provide an electric field in the direction of the connectors. Connectors can be used, for example, to move sample or portions of sample from one lane to another. Connectors can contain electrophoresis gel or other transport medium. Connectors can connect a pair of lanes or any number of lanes; for example, connectors in adjacent barriers can allow transport of material across two, three, four, five, or more lanes. One, two, three, four, five, or more connectors can connect adjacent lanes. Connectors can be perpendicular to lanes; that is, the angle between a connector and a lane can be about 90°. The angle between a connector and a lane can be at least about 10°, 20°, 30°, 40°, 50°, 60°, 70°, 80°, 90°, 100°, 110°, 120°, 130°, 140°, 150°, 160°, or 170°. The angle between a connector and a lane can be at most about 10°, 20°, 30°, 40°, 50°, 60°, 70°, 80°, 90°, 100°, 110°, 120°, 130°, 140°, 150°, 160°, or 170°. The angle between a connector and a lane can be about 10°, 20°, 30°, 40°, 50°, 60°, 70°, 80°, 90°, 100°, 110°, 120°, 130°, 140°, 150°, 160°, or 170°. In some cases, different gel lanes can comprise different types or compositions of gel from each other. Some compositions of gel can have different densities or porosities, which can provide better resolution for specific types or sizes of sample material. For example, a sample comprising DNA molecules from 20 bases to 2000 bases in size can be loaded into a first gel lane; then after some separation (e.g., by an electric field generated by a first pair of electrodes), smaller DNA molecules (e.g., 20 bases to 200 bases) can be shifted (e.g., by an electric field generated by a second pair of electrodes, oriented perpendicularly to the first pair of electrodes) into a second gel lane with higher concentration gel for further higher resolution separation, while separation of larger DNA molecules (e.g., 200 bases to 2000 bases) in the sample continues in the first gel lane. Electrodes and gel composition are discussed further in this disclosure.

An electrophoresis apparatus may include a frame. The frame can be used for casting, shaping, or holding an electrophoresis matrix or gel. The frame may include a bottom surface and one or more side surfaces. The frame may or may not include a top surface. In some instances, the frame may include a bottom surface and four side surfaces extending up from the perimeter of the bottom surface. The bottom surface may have any shape, and the side surfaces may extend upward from the bottom surface along the perimeter of the bottom surface shape. An upper surface of the bottom of the frame may contact a bottom surface of gel or electrophoresis matrix. The top surface of the electrophoresis gel or matrix can be considered the surface of the gel opposite the surface of the gel that contacts the bottom surface.

The electrophoresis matrix can comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 lanes. The electrophoresis matrix can comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 lanes. The electrophoresis matrix may comprise less than any of the number of lanes described, or a number of lanes falling within a range between any two of the values described.

Matrix or gel lanes can comprise different geometrical configurations. Matrix or gel lanes can be parallel with respect to each other. Matrix or gel lanes can be non-parallel with respect to each other. Matrix or gel lanes can have a common width or can vary in width. Matrix or gel lanes can have a common length or can vary in length. Matrix or gel lanes can extend for about 100%, 90%, 80%, 70%, 60%, or 50% of the length of the frame. Matrix or gel lanes can extend for at least about 100%, 90%, 80%, 70%, 60%, or 50% of the length of the frame. Matrix or gel lanes can extend for at most about 100%, 90%, 80%, 70%, 60%, or 50% of the length of the frame. Matrix or gel lanes can have a width of about 0.1, 0.5, 1, 2, 3, 4, 5, 6, 7, 8, 9, 10, 11, 12, 13, 14, 15, 16, 17, 18, 19, 20, 25, 30, 35, 40, 45, or 50 mm. Matrix or gel lanes can have a width of at least about 0.1, 0.5, 1, 2, 3, 4, 5, 6, 7, 8, 9, 10, 11, 12, 13, 14, 15, 16, 17, 18, 19, 20, 25, 30, 35, 40, 45, or 50 mm. Matrix or gel lanes can have a width of at most about 0.1, 0.5, 1, 2, 3, 4, 5, 6, 7, 8, 9, 10, 11, 12, 13, 14, 15, 16, 17, 18, 19, 20, 25, 30, 35, 40, 45, or 50 mm. Matrix or gel lanes can have a length of about 1, 2, 3, 4, 5, 6, 7, 8, 9, 10, 15, 20, 25, 30, 35, 40, 45, or 50 cm. Matrix or gel lanes can have a length of at least about 1, 2, 3, 4, 5, 6, 7, 8, 9, 10, 15, 20, 25, 30, 35, 40, 45, or 50 cm. Matrix or gel lanes can have a length of at most about 1, 2, 3, 4, 5, 6, 7, 8, 9, 10, 15, 20, 25, 30, 35, 40, 45, or 50 cm.

The matrix or gel lanes may be parallel to one or more sides of the frame. The solid barriers may be parallel to one or more sides of the frame. In some instances, the matrix or gel lanes may be perpendicular to one or more sides of the frame. The solid barriers may be perpendicular to one or more sides of the frame. The solid barriers may or may not have a height that is less than or equal to a height of one or more sides of the frame. Alternatively, the solid barriers may have a height that is greater than or equal to the height of one or more sides of the frame.

The matrix or gel can comprise sample loading areas and separation areas. Sample loading areas can comprise wells for holding sample fluids. Sample loading areas (e.g., wells) can receive samples simultaneously, for example from multi-pipette or auto pipette. The spacing and/or sizing of the sample loading areas can be designed to match to the dimensions of a particular loading device, such as a multi-pipette head. Sample loading areas can correspond to, line up with, or be located inside gel lanes, so that material from a particular sample loading area migrates through a particular lane during operation and remains separated from material from other samples.

Various types of sample material can be separated in the matrix or gel, including but not limited to, nucleic acids (e.g., DNA, RNA, PNA), nucleic acid fragments, direct PCR products, proteins (e.g., enzymes, antibodies, structural proteins, storage proteins, transport proteins, motor proteins, hormonal proteins, receptor proteins), protein fragments, peptides, and particles. Different lanes within a gel can be used to separate material of the same type simultaneously. Different lanes within a gel can be used to separate material of different types simultaneously. Different lanes within a gel can be used to separate different size ranges of a material. Enhanced resolution within each of a subset of size ranges of sample material can be provided by the use of different gel compositions tailored for each size range. In some cases, molecules that differ in size or molecular weight by at least 1, 2, 3, 4, or 5 orders of magnitude can be separated and resolved within one gel. For example, nucleic acid molecules between 10 bases and 10 kb can be separated and resolved within one gel. In another example, a sample can comprise three size ranges of sample molecules, and a portion of the sample can be loaded into three gel lanes; the first size range is well-resolved in the first lane, the second size range is well-resolved in the second lane, and the third size range is well-resolved in the third lane. In some instances, molecules may be separated in different lanes at different rates. Molecules may traverse the lanes in different rates. The rates may differ from one another by greater than or equal to about 10%, 20%, 30%, 40%, 50%, 70%, 100%, 150%, 200%, 300%, 400%, 500%, 700%, or 1000%.

Different types of gel can be used, including but not limited to agarose, polyacrylamide, and starch. Gel can be used to separate proteins, nucleic acids, and particles. Polyacrylamide gel can be used to separate nucleic acids, including small fragments of nucleic acids (e.g., about 5-500 bp). Agarose gel can be used to separate proteins, including proteins above about 200 kDa. Agarose gel can be used to separate nucleic acids, including nucleic acids from size about 50 bp up to and including nucleic acids several Mb in size.

Different gel compositions can be used. The porosity of the gel can be affected by the composition of the gel. Different porosity gels can provide improved resolution for particular size ranges of samples. Agarose gel can comprise at least about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% agarose. Agarose gel can comprise at most about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% agarose. Agarose gel can comprise about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% agarose. In some cases, agarose gel can comprise between about 0.7% and about 2% agarose. In some cases, agarose gel can comprise between about 0.7% and about 3% agarose. Polyacrylamide gel can comprise at least about 5%, 6%, 7%, 8%, 9%, 10%, 11%, 12%, 13%, 14%, 15%, 16%, 17%, 18%, 19%, or 20% polyacrylamide. Polyacrylamide gel can comprise at most about 5%, 6%, 7%, 8%, 9%, 10%, 11%, 12%, 13%, 14%, 15%, 16%, 17%, 18%, 19%, or 20% polyacrylamide. Polyacrylamide gel can comprise about 5%, 6%, 7%, 8%, 9%, 10%, 11%, 12%, 13%, 14%, 15%, 16%, 17%, 18%, 19%, or 20% polyacrylamide. In some cases, polyacrylamide gel can comprise between about 6% and about 15% polyacrylamide. For example, between different lanes, the gel composition can vary between lanes by at least about 10%, 20%, 30%, 40%, 50%, 60%, 70%, 80%, 90%, 100%, 110%, 120%, 130%, 140%, 150%, 160%, 170%, 180%, 190%, 200%, 250%, 300%, 350%, 400%, 450%, 500%, 550%, 600%, 650%, or 700%. Between lanes, the gel composition can have porosities differing by one, two, three, four, five or more orders of magnitude. Physical barriers can be used to separate between gel or matrix lanes of different porosities or materials.

A different percentage of polymer or a different mix of polymer can produce a gel especially suited for resolution of a particular size range. For example, 0.7% agarose gel can provide good resolution for nucleic acid fragments between about 5 and 10 kb. For example, 2% agarose gel can provide good resolution for nucleic acid fragments between about 0.2 and 1.0 kb. Gel lanes within an apparatus can be loaded with gels of different or the same type. For example, some gel lanes can be loaded with agarose gel and some lanes can be loaded with polyacrylamide gel. Gel lanes can within an apparatus can be loaded with gels of the same or of different densities or porosities. For example, some gel lanes can be loaded with a 6% polyacrylamide gel while other gel lanes are loaded with a 12% polyacrylamide gel.

Gels can comprise or be used in conjunction with buffers, reagents, detergents, dyes, and other components. Gels can comprise or be used in conjunction with denaturants for nucleic acids, such as urea, DMSO, glyoxal, or methylmercury hydroxide. Gels can comprise or be used in conjunction with denaturants for proteins, such as sodium dodecyl sulfate (SDS), beta-mercaptoethanol or dithiothreitol. Gels can comprise buffers, such as loading buffer, Tris, Bis-Tris, imidazole, EDTA, Tris/Acetate/EDTA (TAE), Tris/Borate/EDTA (TBE), or lithium borate (LB). The buffers used at each electrode can be the same or different. Gels can comprise or be used in conjunction with dyes, including but not limited to, xylene cyanol, Cresol Red, Orange G, bromophenol blue, intercalating dyes (e.g., ethidium bromide, SYBR Green, EvaGreen), and protein stains (e.g., silver stain, Coomassie Brilliant Blue).

Buffer chambers can be shared among all lanes, or a subset of the lanes. Alternatively, each lane can have its own buffer chamber. The buffer chamber configuration can be the same at both ends of the gel or can differ; for example, lanes can share buffer chambers at the top of the gel, while at the bottom of the gel lanes have individual buffer chambers.

Figure 6:
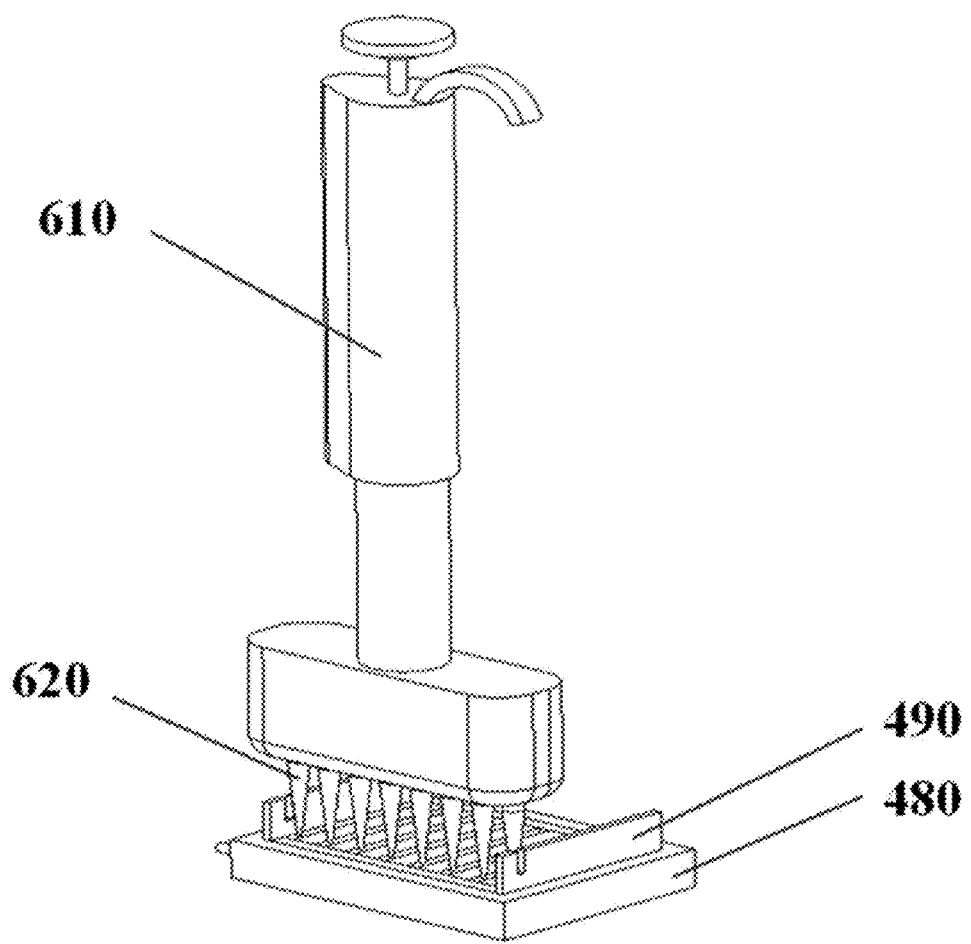
FIG. 6 shows an exemplary schematic of a lane electrophoresis apparatus with a gel casting frame and an auto pipette with pipette tips for delivering fluid.

Gel can be cast with the aid of various tools, such as a gel casting frame or a comb for forming wells. For example, FIG. 4 and FIG. 5 show a lane electrophoresis apparatus 480 with the aid of a gel casting frame 490 and a comb 400. The comb can be used to form wells in the gel for loading sample before the gel solidifies. FIG. 15 and FIG. 16 show a comb 1510 with teeth 1520 which can be used to form wells in a gel. Electrophoresis gel, for example in liquid form, can be added to a lane electrophoresis apparatus with the aid of a pump or other fluid handling equipment. For example, FIG. 6 shows the use of a pump, such as an auto pipette 610 with associated pipette tips 620, to add gel to a lane electrophoresis apparatus 480 or gel casting frame 490. In some cases, the buffer chamber can be filled with buffer prior to adding liquid gel to the lanes, in order to avoid contact between the liquid gel and the electrode. A pump, such as an auto pipette, can also be used for loading samples into wells. Gel can be cast using a gel casting system. For example, FIG. 14 shows a gel casting system comprising a pump 1470, a pipe, tube, or other conduit 1480, a gel injector (e.g., auto pipette) 1490, and a heating zone 1400. Gel can be pre-made or partially pre-made prior to loading; for example, gel or gel precursor can be loaded onto the apparatus but still require some further activation prior to use, such as cross-linking.

The electrophoresis apparatus can comprise electrodes. In some cases, electrodes can be integrated into the electrophoresis apparatus or gel tray, such as in FIG. 1 and FIG. 2. In some cases, electrodes 1040 can be separated from the electrophoresis apparatus 910 or its gel tray, for example as shown in FIG. 10. Electrodes can be shared among all lanes, or a subset of the lanes. Alternatively, each lane can have its own electrode or electrode tip. The electrode configuration can be the same at both ends of the gel or can differ; for example, lanes can share electrodes at the top of the gel, while at the bottom of the gel lanes have individual electrodes.

The electrodes may be positioned to directly contact the gel when the gel is provided within the frame. The electrodes may pass through the trough or chamber for holding buffer or other solutions. The electrodes may or may not contact sides of the frame. The length of the electrodes may be oriented substantially perpendicular to the lengths of the gel lanes. The length of the electrodes may span some or all of the gel lanes. The electrodes may or may not contact the gel. The electrodes may or may not be embedded in the gel. The electrodes may or may not be elevated over a bottom surface of the frame. In some cases, the electrode at the sample loading end of the matrix or gel can be the anode and the electrode at the other end of the matrix or gel can be the cathode. In some cases, the electrode at the sample loading end of the matrix or gel can be the cathode and the electrode at the other end of the matrix or gel can be the anode. In some cases, an electrode can comprise multiple electrode tips, with each tip aligned to a specific lane. The polarity or orientation of electrodes or electrode tips can be the same for all lanes. Alternatively, the polarity or orientation of electrodes or electrode tips can be different for different lanes within the matrix; that is, some lanes can have an anode at the first end and cathodes at the second end while other lanes are oriented in the opposite direction.

The electrophoresis apparatus can comprise multiple sets of electrodes. In some cases, the electrophoresis apparatus can comprise a first set of electrodes and a second set of electrodes oriented orthogonally to the first set of electrodes. The second set of electrodes can be used to transport sample material through connectors between lanes, as described further in this disclosure. For example, FIG. 2B and FIG. 2C show connectors 260, a first vertical set of electrodes 140, and a second horizontal set of electrodes 250. Additional sets of electrodes can be oriented orthogonally to the first set of electrodes. The angle between the orientation of a first set of electrodes and a second set of electrodes can be about 0°, 10°, 20°, 30°, 40°, 50°, 60°, 70°, 80°, 90°, 100°, 110°, 120°, 130°, 140°, 150°, 160°, 170°, or 180°. The angle between the orientation of a first set of electrodes and a second set of electrodes can be at least about 0°, 10°, 20°, 30°, 40°, 50°, 60°, 70°, 80°, 90°, 100°, 110°, 120°, 130°, 140°, 150°, 160°, 170°, or 180°. The angle between the orientation of a first set of electrodes and a second set of electrodes can be at most about 0°, 10°, 20°, 30°, 40°, 50°, 60°, 70°, 80°, 90°, 100°, 110°, 120°, 130°, 140°, 150°, 160°, 170°, or 180°. The voltage supplied to multiple sets of electrodes, or the field strength generated by multiple sets of electrodes, can be the same or can be different between electrode sets.

Optionally, an electrophoresis device may have a detector that may be capable of detecting signals from one or more lanes in real-time. In some instances, the detector may be configured to detect optical signals from the one or more lanes. The detectors may be capable of visually discerning the top surface of the gels in the one or more lanes. Leaving the lanes uncovered may permit the detector to detect optical signals from the top surfaces of the gels in the lane, in real-time. The detector may be capable of detecting optical signals from the gels in multiple lanes simultaneously. The detector may capture an image of the top surfaces of the gels in the multiple lanes. The image may be a still image or may include video-rate images. Optionally, no intermediary materials or covers may be provided between the top surface of the gel and the detector. A direct line of sight may be presented between the top surface of the gel and the detector. In some alternative embodiments, an optically transmissive material may be provided between the gel surface and the detector.

Figure 28A:
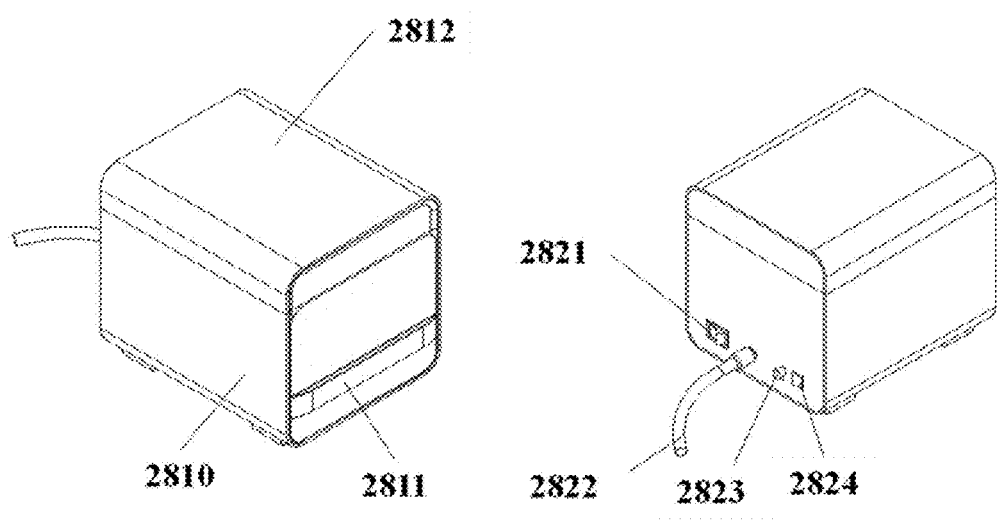
FIG. 28A shows exemplary front and rear three-quarters view schematics of an electrophoresis apparatus with a front slide panel, a top slide panel, a power supply cable, and controls for power and light.
Figure 28B:
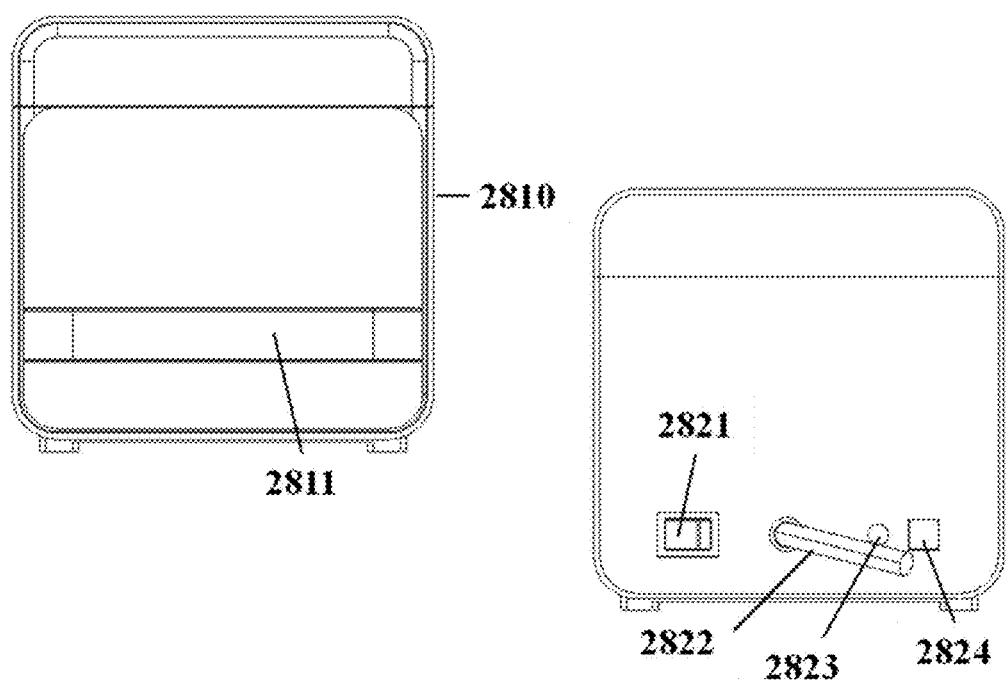
FIG. 28B shows exemplary front and rear elevation view schematics of an electrophoresis apparatus with a front slide panel, a top slide panel, a power supply cable, and controls for power and light.
Figure 28C:
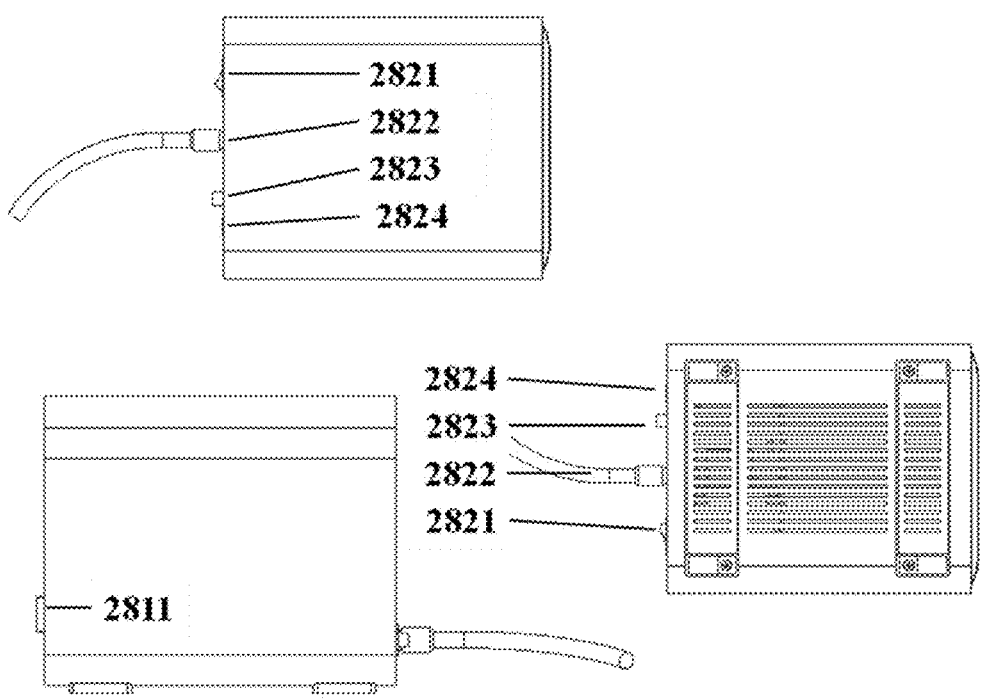
FIG. 28C shows exemplary top, bottom, and right side view schematics of an electrophoresis apparatus with a front slide panel, a top slide panel, a power supply cable, and controls for power and light.
Figure 28D:
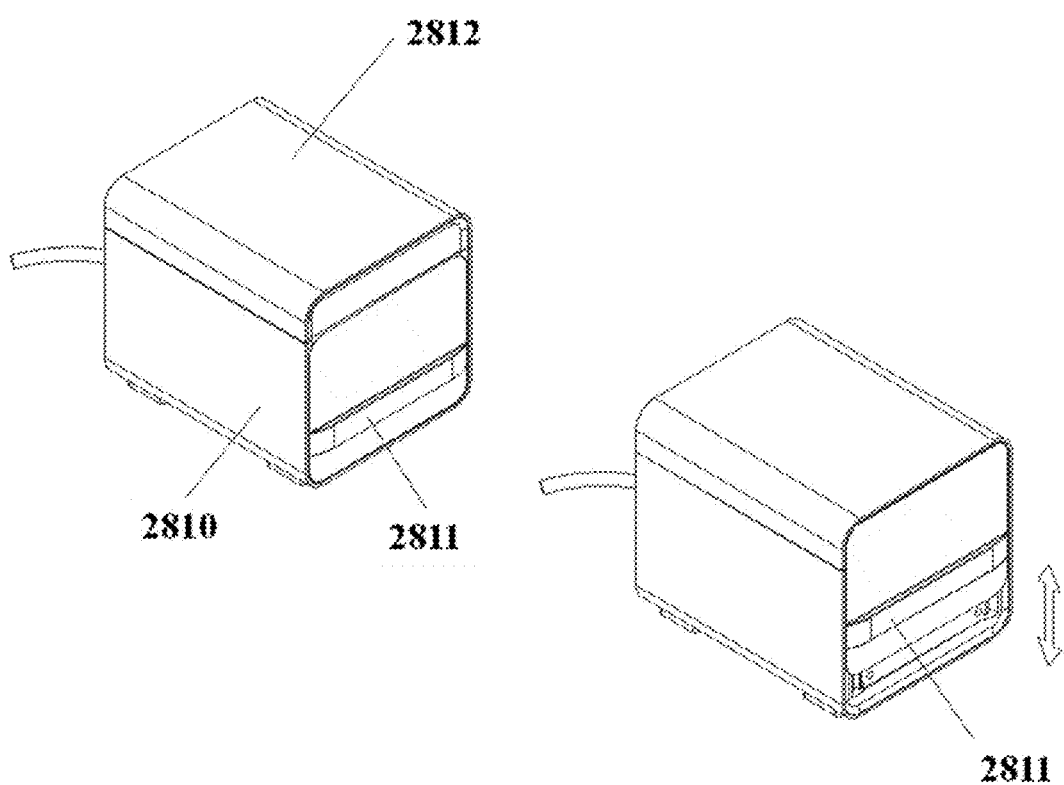
FIG. 28D shows exemplary three-quarters view schematics of an electrophoresis apparatus with a front slide panel in both closed and open configurations.
Figure 28E:
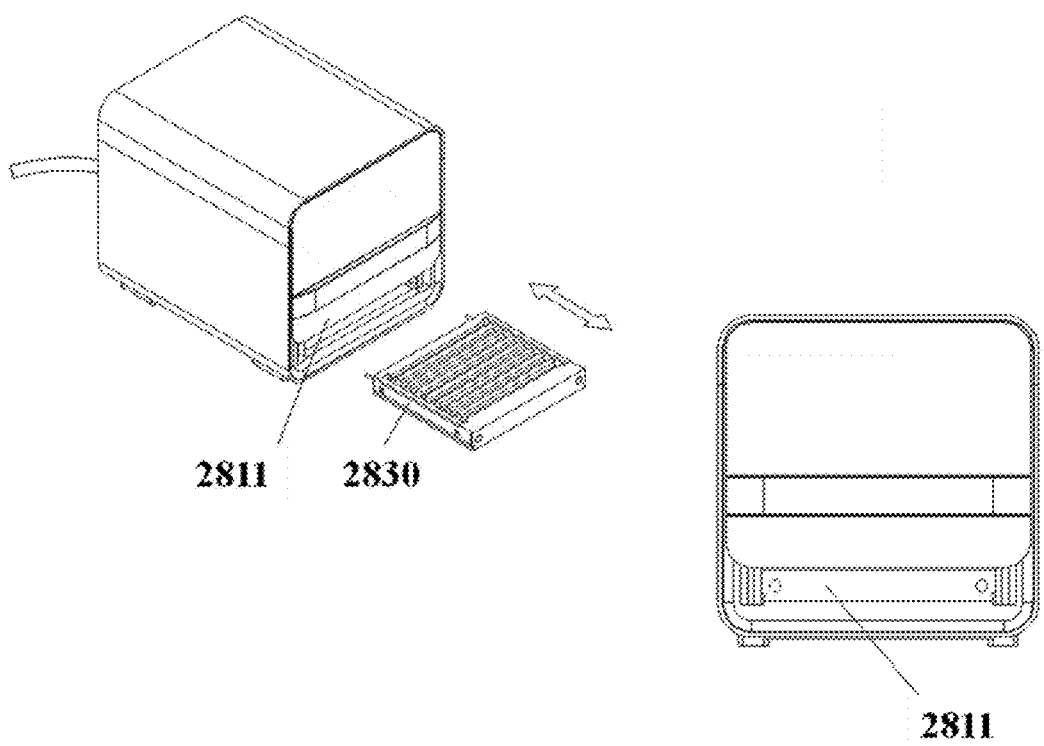
FIG. 28E shows exemplary schematics of an electrophoresis apparatus with a front slide panel being used for electrophoresis matrix loading or unloading.
Figure 28F:
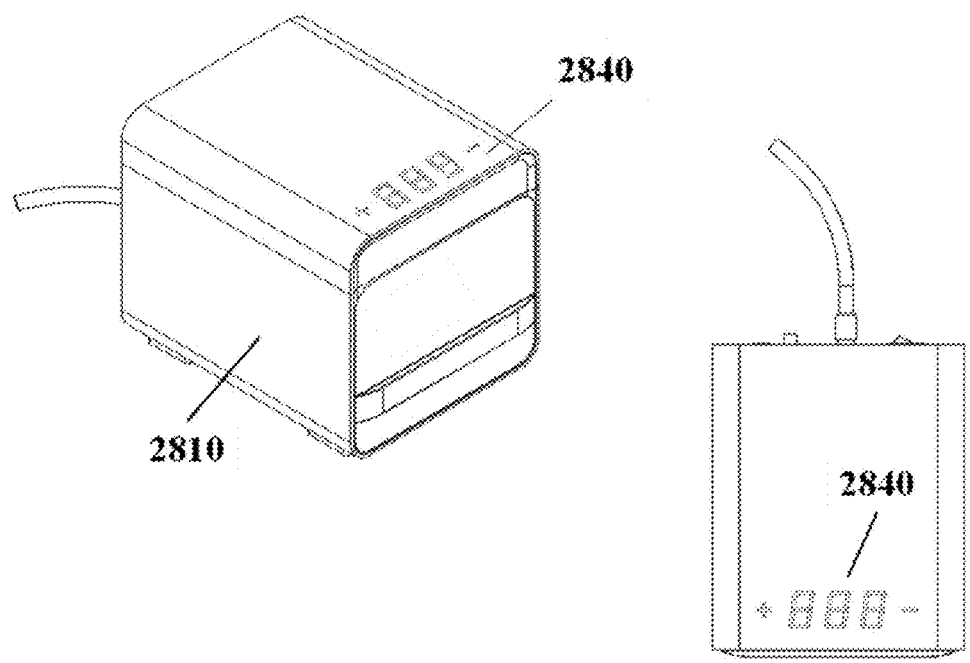
FIG. 28F shows exemplary schematics of an electrophoresis apparatus with a touch control interface.

The electrophoresis apparatus can comprise a drawer or drawer-like structure 1150 with a moveable gel tray 1160, for example as shown in FIG. 11. The drawer can be movable manually or automatically, such as with a motor or actuator. For instance, an actuator may receive a command signal from a controller to cause the drawer to move. The drawer or tray 2830 can be accessible via a panel, such as a sliding panel 2811, for example as shown in FIG. 28D and FIG. 28E. The sliding panel can be movable manually or automatically, such as with a motor or actuator. For instance, an actuator may receive a command signal from a controller to cause the sliding panel to move.

The drawer may move between an open position and a closed position. In some cases, in the open position the matrix or gel is accessible for sample loading. In some cases, in the closed position the matrix or gel is inaccessible for sample loading. In some cases, in the open position the matrix or gel is exposed to elements of the ambient environment. In some cases, in the closed position the matrix or gel is isolated from elements of the ambient environment. Elements of the ambient environment can include but are not limited to light, gas (e.g., air), fluids, liquids, particulates, organisms, viruses, reagents, samples or sample material (e.g., proteins, nucleic acids), light, and temperature.

Figure 19:
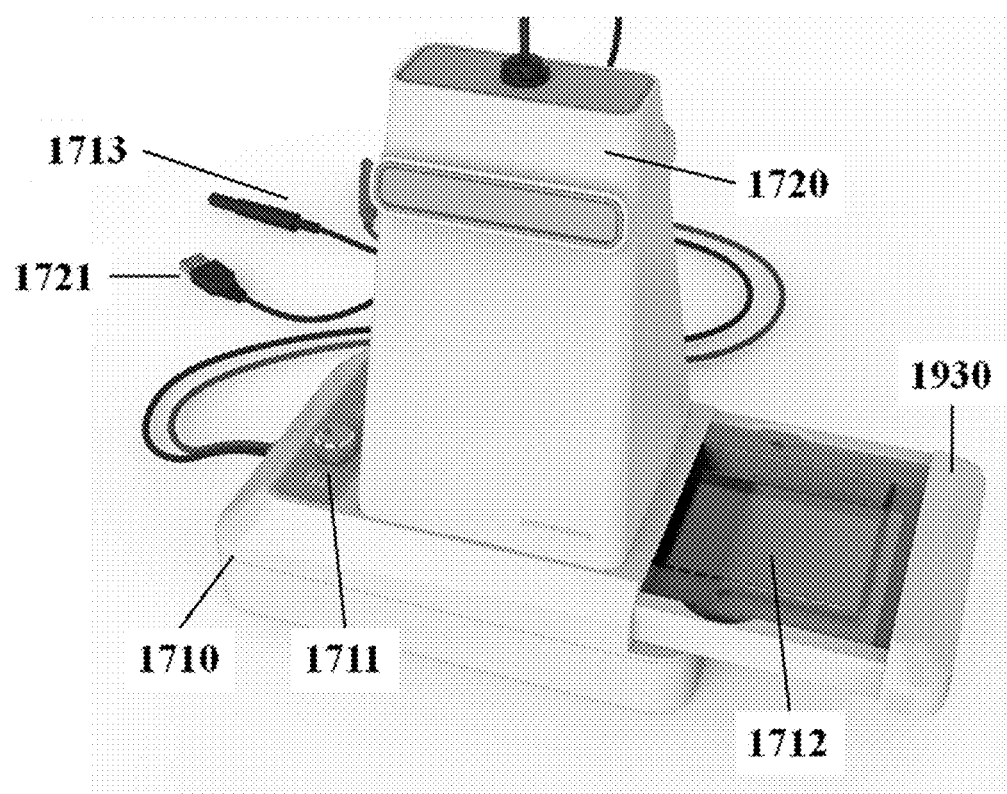
FIG. 19 shows an exemplary drawer-like electrophoresis apparatus with a moveable gel tray.

The motion of the drawer or tray can be entirely or substantially horizontal. The motion of the drawer or tray can be entirely or substantially vertical. The motion of the drawer or tray can include horizontal and vertical elements. The drawer or tray can comprise a lock, stop, or other mechanism to prevent accidental opening. The drawer or tray can be capable of being completely removed from the electrophoresis apparatus. The gel tray 1270 can comprise elements including a buffer trough or chamber 1280, a gel region 1290, sample wells 1200, and electrodes 1210, for example as shown in FIG. 12. The gel tray may include a frame, which can be used to contain or form gel. A cross-section of a gel tray is shown for example in FIG. 13, with a lower gel tray panel 1320, an upper gel tray panel 1330, a buffer stopper or weir 1340, a gel region upper panel 1350, and electrodes 1360. The drawer can be used to access the gel, for example to remove a used gel or add a new gel. For example, FIG. 19 shows a gel tray 1930 slid open from an electrophoresis apparatus 1710 with coupled detector 1720, such that the gel is visible and exposed to the environment, the sample wells are accessible for sample loading, and the gel is physically accessible and can be removed and replaced with a different gel or matrix. The gel or matrix can be removed by hand or with an implement, such as a lever, tweezers, or tongs. The drawer or tray can be capable of being completely removed from the apparatus. If the drawer or tray is completely removed from the apparatus, the gel or matrix can be turned upside down and the gel can be removed with the aid of gravity.

Detector

Figure 28G:
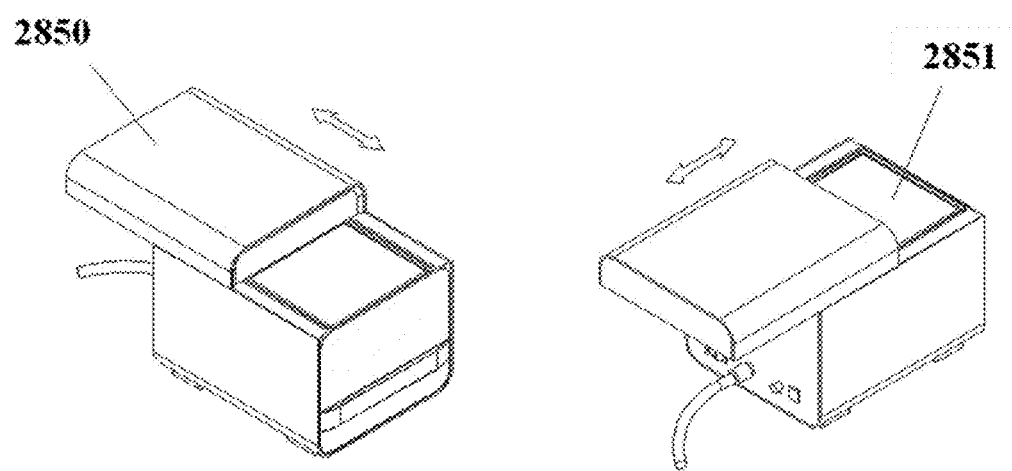
FIG. 28G shows exemplary front and rear three-quarters view schematics of an electrophoresis apparatus with a top slide panel in open configuration for access to an observation window.
Figure 28H:
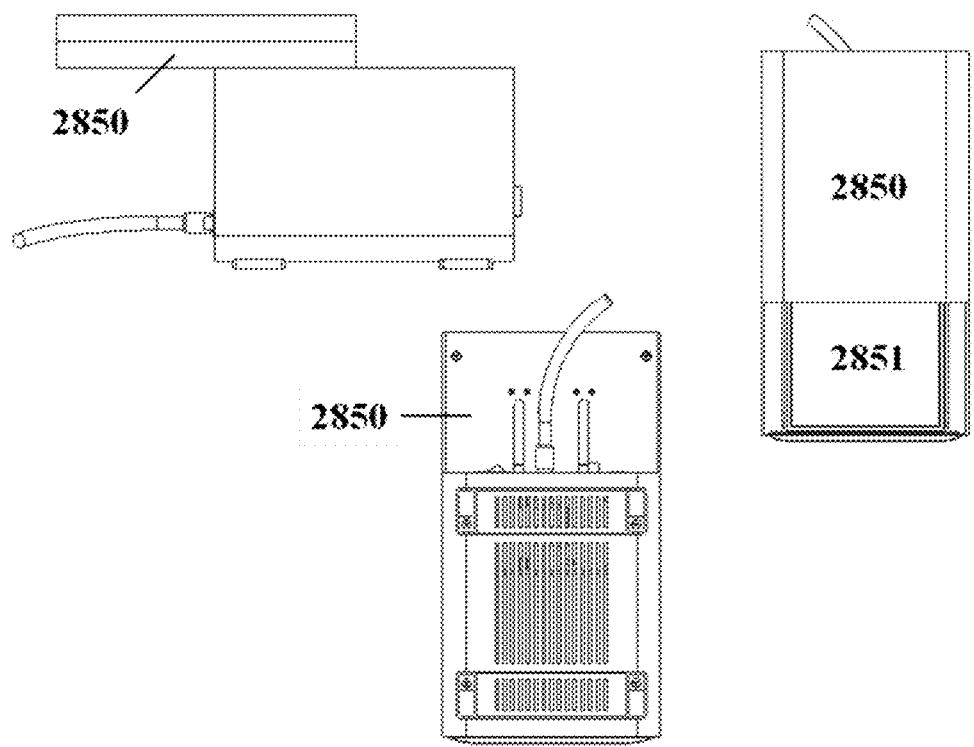
FIG. 28H shows exemplary top, bottom, and left side view schematics of an electrophoresis apparatus with a top slide panel in open configuration.

The electrophoresis apparatus can be used in conjunction with a detector. In some cases, the detector can be integrated within the electrophoresis apparatus housing. For instance, an electrophoresis apparatus housing may enclose the detector. The electrophoresis apparatus housing may enclose the detector, along with one or more gel lanes. The electrophoresis apparatus housing may enclose the detector and the matrix or gel. The electrophoresis apparatus housing may enclose the detector, the matrix or gel, and a power supply. The electrophoresis apparatus housing may enclose the detector, a light source, and the matrix or gel. The electrophoresis apparatus housing may enclose the detector, a light source, the matrix or gel, and a power supply. The electrophoresis apparatus housing may enclose the detector, communications equipment, and the matrix or gel. The electrophoresis apparatus housing may enclose the detector, communications equipment, the matrix or gel, and a power supply. The electrophoresis apparatus housing may enclose the detector, communications equipment, a light source, and the matrix or gel. The electrophoresis apparatus housing may enclose the detector, communications equipment, a light source, the matrix or gel, and a power supply. In some cases, the detector can be enclosed within its own housing. The detector housing can enclose the detector and a light source. The detector housing can enclose the detector and communications equipment. The detector housing can enclose the detector, a light source, and communications equipment. The detector can be located in a sliding panel, such as a top sliding panel 2850 providing access to an observation window 2851, for example as shown in FIG. 28G and FIG. 28H. In some cases, a sliding panel enclosing the detector can be positioned in an open state for external viewing of the electrophoresis matrix (e.g., via observation window) or positioned in a closed state for imaging of the electrophoresis matrix with the detector. The sliding panel can be movable manually or automatically, such as with a motor or actuator. For instance, an actuator may receive a command signal from a controller to cause the sliding panel to move.

Figure 17:
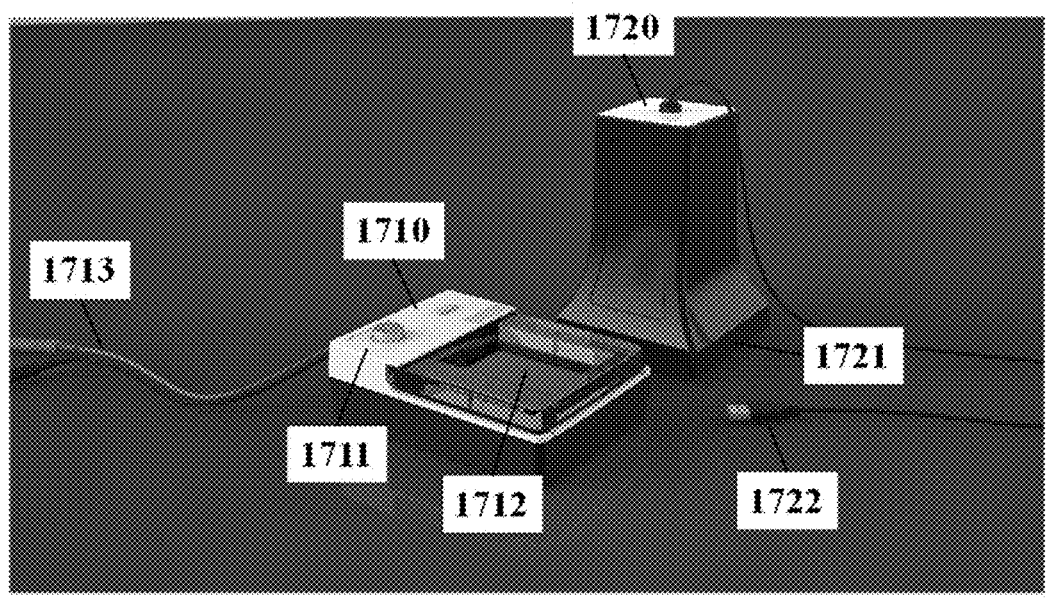
FIG. 17 shows an exemplary electrophoresis apparatus and an imaging system.
Figure 18:
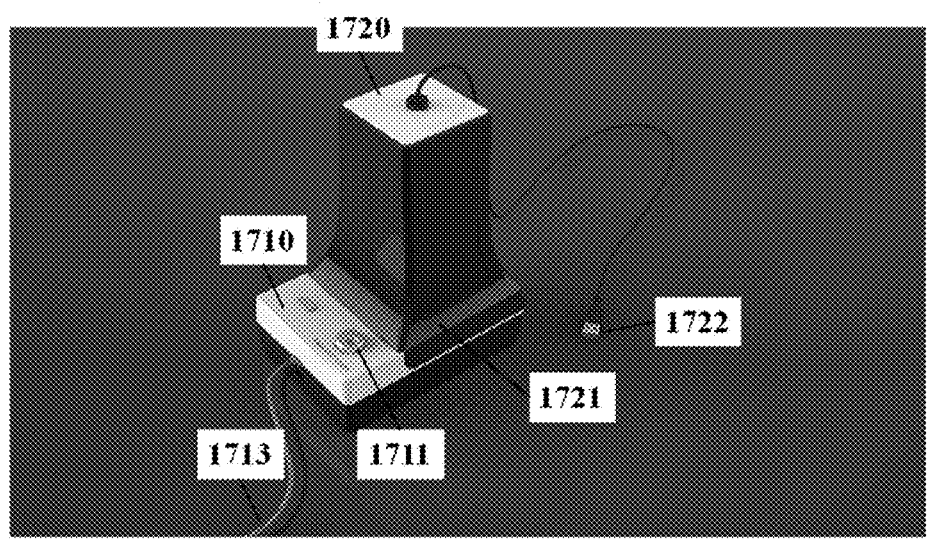
FIG. 18 shows an exemplary imaging system mounted to an electrophoresis apparatus.

Alternatively, the detector can be contained in its own separate housing. For example, FIG. 17, FIG. 18, FIG. 19, FIG. 20, and FIG. 22 show a detector 1720 in its own housing but coupled to or capable of being coupled to the electrophoresis apparatus 1710. The detector housing can be coupled to the electrophoresis housing. The detector housing can be attached in a removable manner to the electrophoresis housing. The coupling between the detector housing and the electrophoresis housing can prevent all or most ambient light from reaching the gel or the detector. The detector housing can comprise a shade, sleeve, or other fixture to shield the interior of the detector housing and/or electrophoresis housing from environmental light, for example as shown in FIG. 17 (1721), FIG. 18 (1721), and FIG. 22 (2221).

The detector can comprise an image sensor or image sensors. The image sensor can be capable of optical detection. The image sensor can comprise a charge-coupled device (CCD) sensor, including a cooled CCD. The image sensor can comprise an active-pixel sensor (APS), such as a CMOS or NMOS sensor. The detector can comprise a laser sensor. The detector can comprise a photodiode, such as an avalanche photodiode. The detector can comprise a photomultiplier tube (PMT). The sensors can comprise a single sensor or multiple sensors, of the same type or of different types.

The detector can image subjects, such as a matrix or a region of a matrix. The detector can image at least 10%, 20%, 30%, 40%, 50%, 60%, 70%, 80%, 90%, 95%, or 100% of the matrix in one field of view. The detector can image subjects before, during, or after operation of the electrophoresis apparatus. The detector can image in real-time while the electrophoresis apparatus is operating, for example during the electrophoretic separation of sample material with a matrix.

The detector can record single still images or can record video. The detector can sample at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, or 300 times per minute. The detector can sample at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, or 300 times per minute. The detector can sample about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, or 300 times per minute. The detector can sample at a rate of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 15, 20, 25, 30, 35, 40, 45, 50, 55, 60, 65, 70, 75, 80, 85, 90, 95, 100, 105, 110, 115, or 120 Hz. The detector can sample at a rate of at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 15, 20, 25, 30, 35, 40, 45, 50, 55, 60, 65, 70, 75, 80, 85, 90, 95, 100, 105, 110, 115, or 120 Hz. The detector can sample at a rate of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 15, 20, 25, 30, 35, 40, 45, 50, 55, 60, 65, 70, 75, 80, 85, 90, 95, 100, 105, 110, 115, or 120 Hz.

The detector can have particular resolution or sensitivity. The detector can comprise at least about 100, 200, 500, 1000, 2000, 3000, 4000, 5000, 6000, 7000, 8000, 9000, or 10,000 pixels on a side. The detector can comprise at least about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 megapixels. The detector can have a resolution of at least about 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, 0.009 mm, 0.008 mm, 0.007 mm, 0.006 mm, 0.005 mm, 0.004 mm, 0.003 mm, 0.002 mm, 0.001 mm, 900 nm, 800 nm, 700 nm, 600 nm, 500 nm, 400 nm, 300 nm, 250 nm, 200 nm, or 100 nm. The detector can have a resolution of at most about 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, 0.009 mm, 0.008 mm, 0.007 mm, 0.006 mm, 0.005 mm, 0.004 mm, 0.003 mm, 0.002 mm, 0.001 mm, 900 nm, 800 nm, 700 nm, 600 nm, 500 nm, 400 nm, 300 nm, 250 nm, 200 nm, or 100 nm. The detector can have a resolution of about 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, 0.009 mm, 0.008 mm, 0.007 mm, 0.006 mm, 0.005 mm, 0.004 mm, 0.003 mm, 0.002 mm, 0.001 mm, 900 nm, 800 nm, 700 nm, 600 nm, 500 nm, 400 nm, 300 nm, 250 nm, 200 nm, or 100 nm.

The detector can comprise a light source. The light source can be integrated into the detector housing or the electrophoresis apparatus housing. The light source can comprise a lamp, such as an incandescent, halogen, fluorescent, gas-discharge, arc, or LED lamp. The light source can comprise a laser. The light source can produce a specific wavelength or range or wavelengths, such as UV. The light source can comprise filters for controlling the output wavelength or wavelengths. The light source can comprise multiple light sources, of the same or of different types, which can be used separately or in combination. The light source can be enclosed by its own housing or by the electrophoresis apparatus housing.

The detector can comprise various optical elements, including but not limited to filters, lenses, collimators, mirrors, reflectors, beam splitters, and diffusers. A matrix or gel can be exposed to light, for example light from a light source. Light can pass through one or more optical elements between the light source and the matrix, or light can travel directly from the light source to the matrix. The detector can receive light from the matrix. Light can pass through one or more optical elements between the matrix and the detector, or light can travel directly from the matrix to the detector. Light can be collimated. Light may be evenly distributed over multiple gel lanes. The multiple gel lanes may be illuminated with light of substantially equal intensity. Light may be directed in a manner to be substantially perpendicular to the gel upper surface. Light can be multi-directional. Light can comprise one wavelength, a narrow band of wavelengths, a broad band of wavelengths, or a full spectrum. Light can comprise visible light wavelengths. Light can comprise ultraviolet wavelengths. Light can comprise infrared wavelengths. Light can be focused by a lens. Images produced by the detector can comprise bright field images. Images produced by the detector can comprise dark field images. Images produced by the detector can comprise fluorescent images.

The detector can comprise a filter or filters, including but not limited to wavelength filters (e.g., color filters, UV filters, IR filters), dichroic filters, and polarizing filters. The filters can comprise multiple filters, of the same or of different types, which can be used separately or in combination.

The detector can comprise a lens or lenses. The lens can be a macro or "close-up" lens. The lens can be a zoom lens. The lens can be an infrared lens. The lens can be an ultraviolet lens. The lens can be a wide angle lens, including but not limited to wide angle lenses, ultra wide angle lenses, and fisheye lenses. The lenses can comprise multiple lenses, of the same or different types, which can be used separately or in combination.

The detector can comprise means for removing image distortion or aberration, such as barrel or fisheye distortion, pincushion distortion, mustache distortion, monochromatic aberrations (e.g., piston, tilt, defocus, spherical aberration, coma, astigmatism, field curvature, image distortion), or chromatic aberrations (e.g., axial, longitudinal, lateral, transverse). Such means can comprise computer systems programmed to implement instructions for partially or fully correcting image distortion. For example, Brown's distortion model or the Brown-Conrady model can be used to correct for radial distortion and tangential distortion.

The detector can comprise communication equipment, such as wired (e.g., USB) or wireless (e.g., Wi-Fi, Bluetooth) communication equipment. The communication equipment can comprise equipment for radio. The communication equipment can comprise equipment for free-space optical (FSO) communication, such as visible or infrared (IR) communication. The communication equipment can comprise equipment for wired communication, including but not limited to universal serial bus (USB), fiber-optics, peripheral component interconnect (PCI), PCI Express (PCIe), or Thunderbolt. The communication equipment can comprise equipment for Wi-Fi, such as IEEE 802.11 a, b, g, or n Wi-Fi. The communication equipment can comprise equipment for cellular data service, such as GSM, CDMA, GPRS, 3G, (e.g., W-CDMA, EDGE, CDMA2000), or 4G (e.g., Long Term Evolution (LTE), Mobile WiMAX). The communication equipment can comprise equipment for mobile satellite communications. The communication equipment can comprise equipment for Bluetooth communication. The communication equipment can comprise multiple types of communication equipment, such as USB and Wi-Fi, or Bluetooth and Wi-Fi.

The communication equipment can transmit information from the detector, such as images recorded by the detector (e.g., images of a gel). The communication equipment can transmit information, such as images, in real time. The communication equipment can communicate with the electrophoresis apparatus and/or control systems thereof. The communication equipment can communicate with remote computer systems, such as desktop computers, laptop computers, tablet computers, smartphone devices, or servers. The communication equipment can communicate with display devices, such as handheld display devices. The communication equipment can transmit information, such as images, to a user at a separate location or facility.

Remote Monitoring

The electrophoresis apparatus can comprise equipment for the remote monitoring and control of operations and results. Information can be transmitted between the electrophoresis apparatus 2510 and a remote device 2520 over a network 2530, for example as shown in FIG. 25. Alternatively, information can be transmitted between the electrophoresis apparatus 2610 and a remote device 2620 directly, via wired or wireless communications, for example as shown in FIG. 26. In some instances, the networks may be local area networks (LAN) or wide area networks (WAN), such as the Internet. The networks may optionally be telecommunications networks, such as GSM, 3G, or 4G networks. Additional networks and communications are further discussed elsewhere in this disclosure.

The apparatus can comprise communication equipment, such as wired 2941 (e.g., USB) or wireless 2942 (e.g., Wi-Fi, Bluetooth) communication equipment (e.g., FIG. 29). The communication equipment can comprise equipment for radio. The communication equipment can comprise equipment for free-space optical (FSO) communication, such as visible or infrared (IR) communication. The communication equipment can comprise equipment for wired communication, including but not limited to universal serial bus (USB), fiber-optics, peripheral component interconnect (PCI), PCI Express (PCIe), or Thunderbolt. The communication equipment can comprise equipment for Wi-Fi, such as IEEE 802.11 a, b, g, or n Wi-Fi. The communication equipment can comprise equipment for cellular data service, such as GSM, CDMA, GPRS, 3G, (e.g., W-CDMA, EDGE, CDMA2000), or 4G (e.g., Long Term Evolution (LTE), Mobile WiMAX). The communication equipment can comprise equipment for mobile satellite communications. The communication equipment can comprise equipment for Bluetooth communication.

The communication equipment can transmit information from the apparatus, such as operational data (e.g., voltage, field strength, running time) or images recorded by the detector (e.g., images of a gel). The communication equipment can receive information, such as commands to start operation, stop operation, or change operational conditions. Communication equipment can transmit information from the apparatus and/or detector, such as imaging data (e.g., images or videos) or operational data (e.g., voltage, field strength, run time). Communication equipment can transmit information in real time, or on a delay. Communication equipment can be used to provide instructions to the apparatus and/or detector, such as instructions to begin electrophoresis, stop electrophoresis, alter the applied voltage or electric field strength, take an image or video, transmit an image or video, begin taking images or videos at a specified time or rate, alter the imaging rate, or stop taking images or videos. Instructions can be given to be carried out immediately or at a future time. In some instances, instructions may be provided by a user via a user interface. The user may be remote user. Alternatively, instructions may be generated with aid of one or more processors. An automated or semi-automated system may be provided that may generate instructions off-board the electrophoresis apparatus. The communication equipment can transmit and receive information in real time. The communication equipment can communicate with remote computer systems, such as desktop computers, laptop computers, tablet computers, smartphone devices, or servers. The communication equipment can communicate with display devices, such as handheld display devices. The communication equipment can communicate with various devices, including but not limited to a laptop computer 2931, a desktop computer 2932, or a mobile device 2933 (e.g., FIG. 29).

The communication equipment can transmit and receive information to/from a user at a separate location or facility. The separate location or facility can be located in a different room. The separate location or facility can be located in a different city. The separate location or facility can be located in a different state. The separate location or facility can be located in a different country. The separate location or facility can be located on a different continent. The separate location or facility can be located in a different time zone. The separate location or facility can be at least 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000, or 20,000 km away.

Physical Shape

The electrophoresis apparatus housing can comprise different shapes and form factors, for example as shown in FIG. 17-23. Imaging or detecting equipment 1720 can be located in a separate housing from the electrophoresis apparatus 1710 (e.g., FIG. 17), and can be configured to mount onto the electrophoresis apparatus for imaging (e.g., FIG. 18). The apparatus can comprise a control interface 1711. The control interface may permit a user to interact directly with the device. For example, the user may turn the device on or off, or control one or more aspects of the electrophoresis and/or detection. The apparatus can comprise a matrix 1712. The matrix may be part of a lower base or body of the electrophoresis apparatus. The apparatus can comprise power cables or connectors 1713. The power cables or connectors may provide power from an external power source. Optionally, the external power source may be a low voltage power source, such as a 24 V or 12 V power source, or any other voltage value mentioned elsewhere herein. The apparatus or detector housing can comprise a shield, sleeve, or other structure to block outside light 1721. The apparatus or detector can comprise communications equipment, cables, or connectors 1722. The connectors may optionally connect to a lower base of the electrophoresis apparatus or an external device. Data collected by the detector may be transmitted wirelessly directly to the base or to an external device. Alternatively, data collected by the detector may be transferred via a wireless connection to the base. The base may optionally transmit data from the detector to an external device via a wired or wireless connection.

The electrophoresis apparatus housing can comprise a sliding gel tray (e.g., 1930, 2830) as previously described (e.g., FIG. 19, FIG. 28E). The sliding gel tray may move laterally relative to a base of the electrophoresis device. Detection apparatus 1720 may be permitted to remain attached while the gel tray moves laterally. Thus, the matrix 1712 may be accessed by a user without having to remove the detection apparatus.

Figure 20:
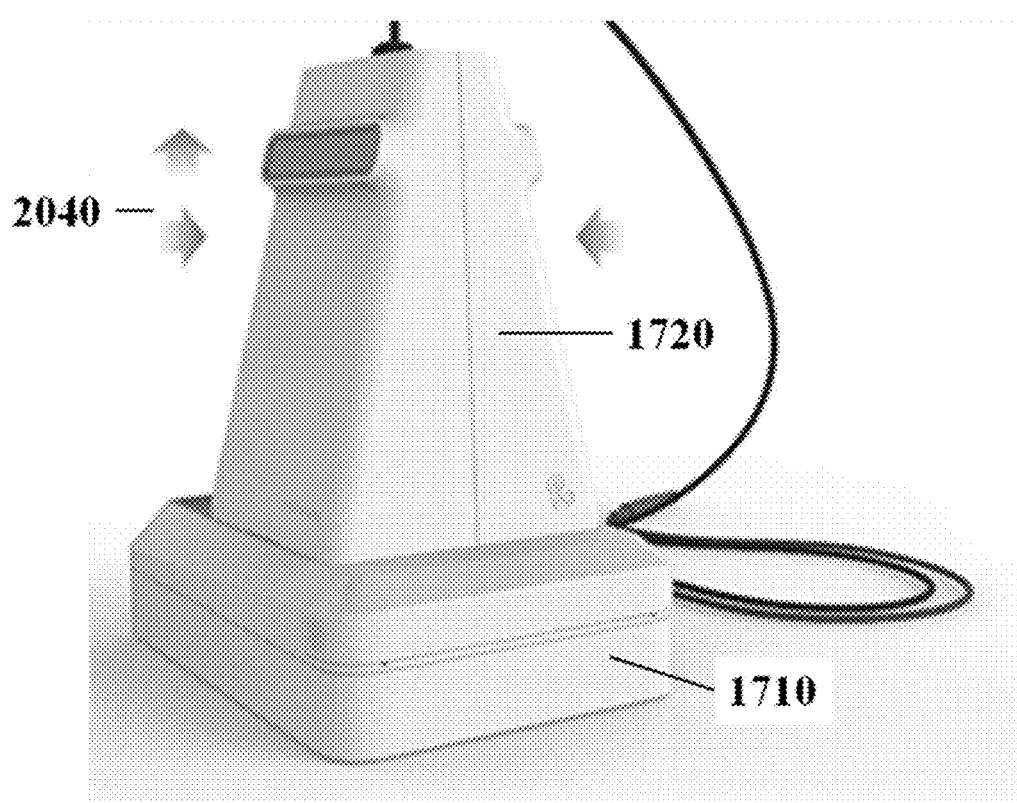
FIG. 20 shows an exemplary imaging system mounted to an electrophoresis apparatus.

The mounting of the imaging or detecting equipment 1720 can utilize a variety of methods or motions 2040 (e.g., FIG. 20, FIG. 28G). For instance, the detecting equipment may move laterally and/or vertically relative to the electrophoresis apparatus base 1710. This motion may be provided to attach and/or detach the detecting equipment from the electrophoresis apparatus base.

Figure 21:
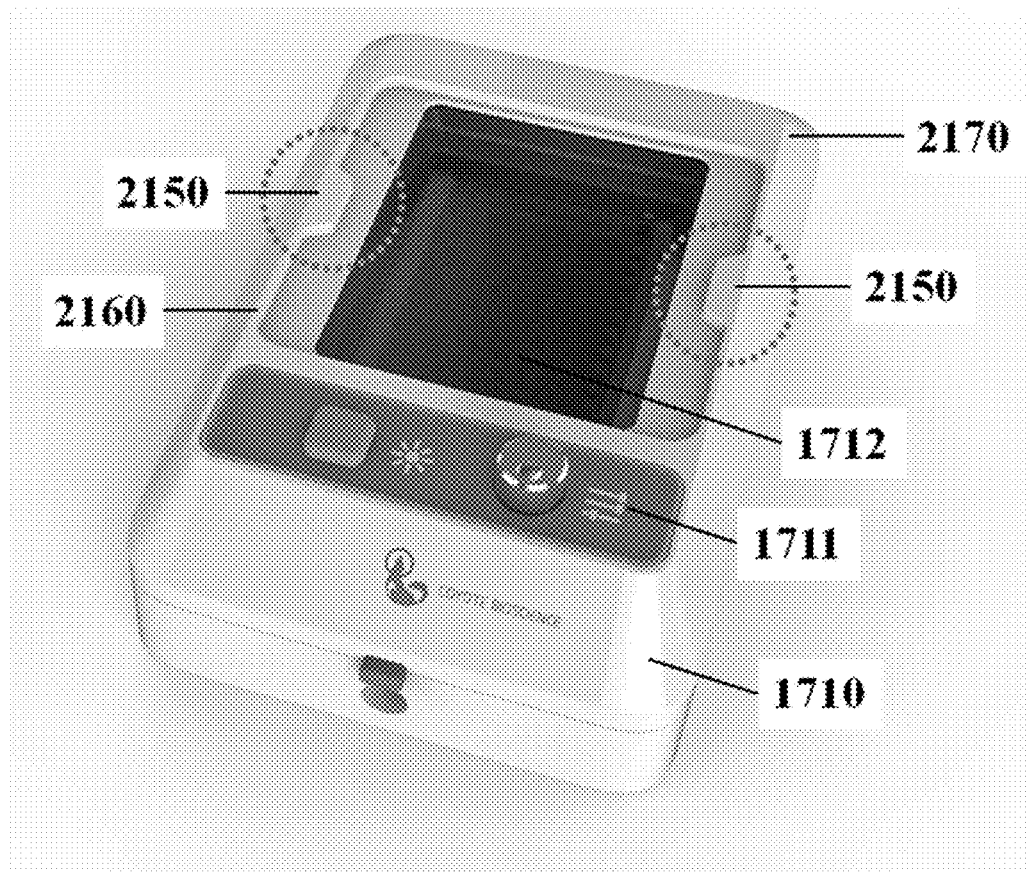
FIG. 21 shows an exemplary electrophoresis apparatus.

Mounting can be aided by connectors, tabs, or other adaptors 2150 on the apparatus housing (e.g., FIG. 21). For example, tabs may protrude from an electrophoresis apparatus 1710 housing and may mate with portions of detection equipment that may be configured to attach to the electrophoresis apparatus. The detection equipment apparatus may include portions that may slide underneath the tabs and be held in place by the tabs. The detection equipment may fit into a perimeter 2160 from which the tabs extend. Optionally, a shoulder 2170 may be provided upon which the detection equipment may rest.

Figure 22:
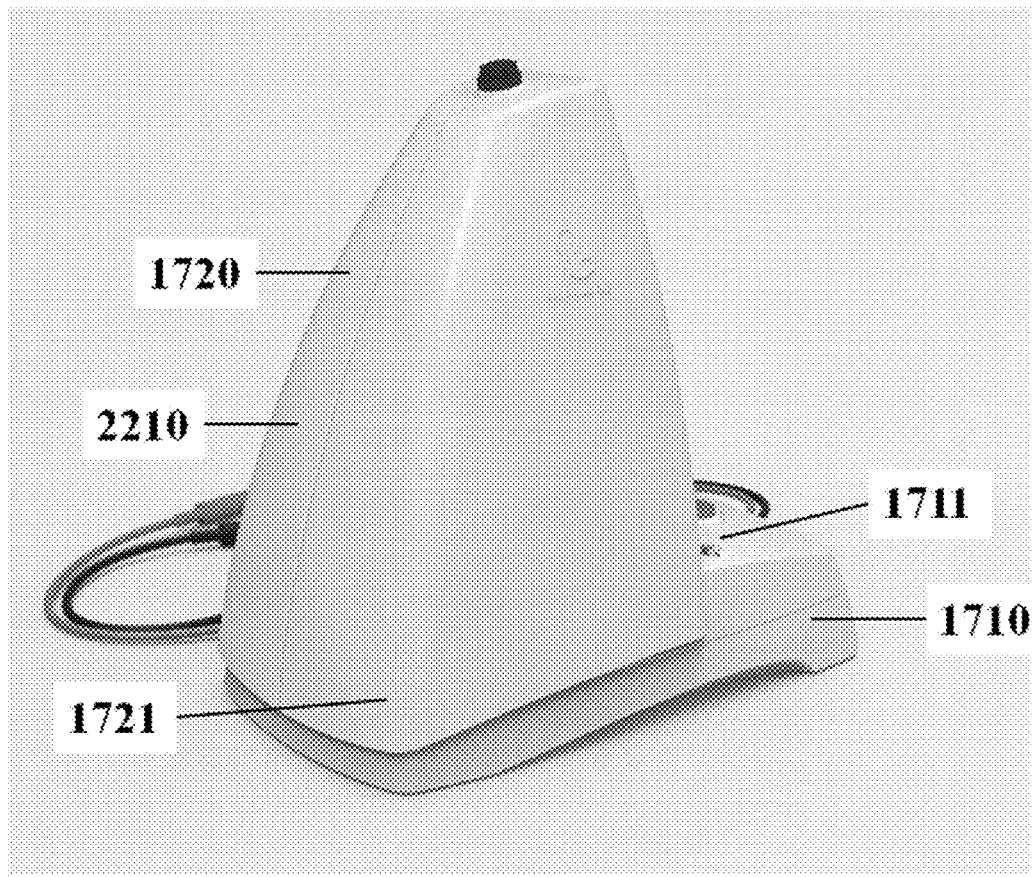
FIG. 22 shows an exemplary electrophoresis apparatus with a mounted imaging system.

The imaging or detector equipment housing can comprise different shapes and form factors 2210 (e.g., FIG. 22). In some instances, the detector equipment may have a curved surface (e.g., concave or convex) or a straight surface. The detector equipment may have a greater height than width, or vice versa.

Figure 23:
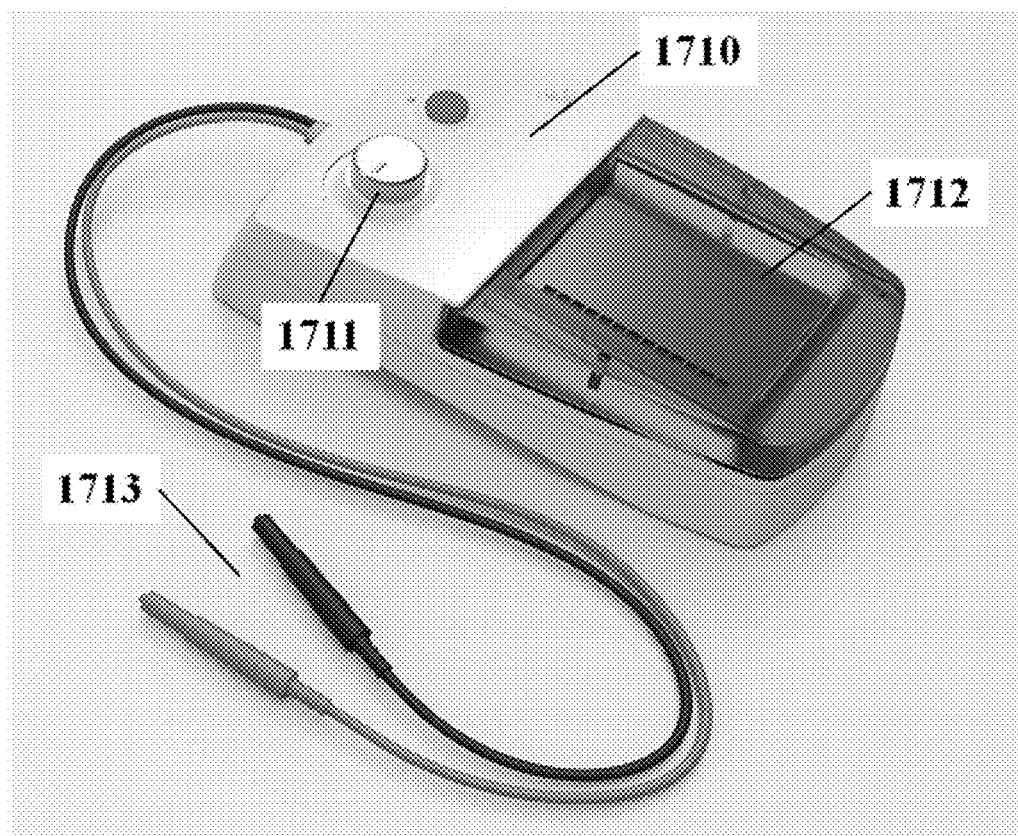
FIG. 23 shows an exemplary integrated electrophoresis apparatus and power supply.

The form factor of the electrophoresis housing can be small (e.g., FIG. 23). In some instances, the electrophoresis housing may be substantially flat, or may have a smaller height than width. A control interface 1711, gel 1712, and/or connector 1713 may be provided. The electrophoresis housing may have any of the dimensions described elsewhere herein for an electrophoresis device.

Figure 27:
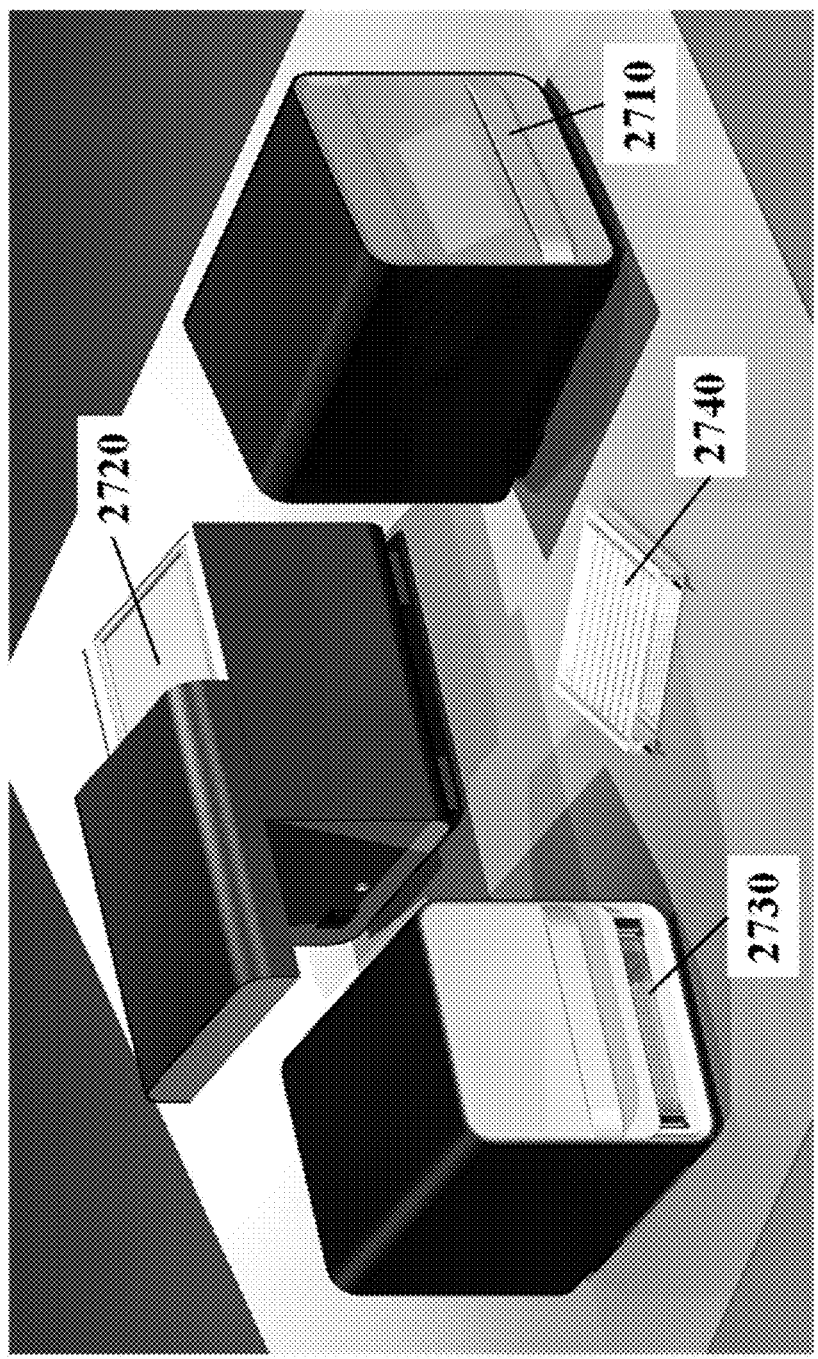
FIG. 27 shows an exemplary electrophoresis apparatus with a front slide panel for electrophoresis matrix access and a top slide panel for access to an observation window.

The electrophoresis apparatus housing can comprise one or more sliding panels 2710 2730, allowing access to various components such as an observation window 2720 or a gel matrix tray 2740 (e.g., FIG. 27). A sliding panel can be movable manually or automatically, such as with a motor or actuator. For instance, an actuator may receive a command signal from a controller to cause a sliding panel to move.

The electrophoresis apparatus housing can comprise one or more controls, such as a main switch 2821, a light tuning control 2823, a light power switch 2824, or a voltage control 2840 (e.g., FIG. 28A, FIG. 28B, FIG. 28C, FIG. 28F). In some cases, a control can be visible only when the apparatus power is on (e.g. 2840 FIG. 28F).

Some or all of the components necessary for conducting electrophoresis can be integrated within the electrophoresis apparatus housing. For example, the gel tray and power supply can both be integrated into the same housing. A light source for imaging or detection can be integrated within the apparatus housing. Communications equipment, such as wireless (e.g., Wi-Fi, Bluetooth) or wired (e.g., USB) communication equipment, can be integrated within the housing. The electrophoresis apparatus housing may enclose the detector and the matrix or gel. The electrophoresis apparatus housing may enclose the detector, the matrix or gel, and a power supply. The electrophoresis apparatus housing may enclose the detector, a light source, and the matrix or gel. The electrophoresis apparatus housing may enclose the detector, a light source, the matrix or gel, and a power supply. The electrophoresis apparatus housing may enclose the detector, communications equipment, and the matrix or gel. The electrophoresis apparatus housing may enclose the detector, communications equipment, the matrix or gel, and a power supply. The electrophoresis apparatus housing may enclose the detector, communications equipment, a light source, and the matrix or gel. The electrophoresis apparatus housing may enclose the detector, communications equipment, a light source, the matrix or gel, and a power supply. The electrophoresis apparatus housing may enclose the matrix or gel. The electrophoresis apparatus housing may enclose the matrix or gel, and a power supply. The electrophoresis apparatus housing may enclose a light source, and the matrix or gel. The electrophoresis apparatus housing may enclose a light source, the matrix or gel, and a power supply. The electrophoresis apparatus housing may enclose communications equipment, and the matrix or gel. The electrophoresis apparatus housing may enclose communications equipment, the matrix or gel, and a power supply. The electrophoresis apparatus housing may enclose communications equipment, a light source, and the matrix or gel. The electrophoresis apparatus housing may enclose communications equipment, a light source, the matrix or gel, and a power supply.

In some cases, the electrophoresis apparatus housing can have a maximum height of less than about 50 cm, 45 cm, 40 cm, 30 cm, 25 cm, or 20 cm, 15 cm, 10 cm, or 5 cm. In some cases, the electrophoresis apparatus housing can have a height of less than about 30 cm. In some cases, the electrophoresis apparatus housing can have a maximum dimension (e.g., height, length, width, diagonal, or diameter) of less than about 30 cm, 25 cm, 20 cm, 15 cm, or 10 cm. In some cases, the electrophoresis apparatus housing can have a lateral dimension (e.g., width, length) of less than about 30 cm, 25 cm, 20 cm, 15 cm, or 10 cm. In some cases, the electrophoresis apparatus housing can have a lateral dimension (e.g., width, length) of less than about 10 cm. In some cases, the electrophoresis apparatus housing can have a height to width ratio of less than about 2, 1.9, 1.8, 1.7, 1.6, 1.5, 1.4, 1.3, 1.2, 1.1, 1.0, 0.9, 0.8, 0.7, 0.6, or 0.5. In some cases the electrophoresis apparatus can have a height to width ratio of less than about 1.

In some cases, the electrophoresis apparatus can have a maximum mass of less than about 10 kg, 9 kg, 8 kg, 7 kg, 6 kg, 5 kg, 4 kg, 3 kg, 2 kg, 1 kg, 0.9 kg, 0.8 kg, 0.7 kg, 0.6 kg, or 0.5 kg. In some cases, the electrophoresis apparatus and detector can have a combined maximum mass of less than about 20 kg, 19 kg, 18 kg, 17 kg, 16 kg, 15 kg, 14 kg, 13 kg, 12 kg, 11 kg, 10 kg, 9 kg, 8 kg, 7 kg, 6 kg, 5 kg, 4 kg, 3 kg, 2 kg, 1 kg, 0.9 kg, 0.8 kg, 0.7 kg, 0.6 kg, or 0.5 kg.

In some cases, the electrophoresis apparatus can have a small footprint, that is the horizontal surface area or the area of a surface covered when the apparatus is placed on that surface. In some cases, the electrophoresis apparatus can have a footprint of less than or equal to about 2000, 1900, 1800, 1700, 1600, 1500, 1400, 1300, 1200, 1100, 1000, 900, 800, 700, 600, 500, 450, 400, 350, 300, 250, 200, 150, 100, 90, 80, 70, 60, or 50 $cm^2$. In some cases, the electrophoresis apparatus can have a footprint between about 100 and 1000 $cm^2$. In some cases, the electrophoresis apparatus can have a footprint between about 200 and 1000 $cm^2$. In some cases, the electrophoresis apparatus can have a footprint between about 250 and 1000 $cm^2$. In some cases, the electrophoresis apparatus can have a footprint between about 300 and 1000 $cm^2$. In some cases, the electrophoresis apparatus can have a footprint between about 100 and 900 $cm^2$. In some cases, the electrophoresis apparatus can have a footprint between about 100 and 800 cm². In some cases, the electrophoresis apparatus can have a footprint between about 100 and 700 cm². In some cases, the electrophoresis apparatus can have a footprint between about 100 and 600 cm². In some cases, the electrophoresis apparatus can have a footprint between about 100 and 500 cm². In some cases, the electrophoresis apparatus can have a footprint between about 100 and 400 cm². In some cases, the electrophoresis apparatus can have a footprint between about 100 and 300 cm². In some cases, the electrophoresis apparatus can have a footprint between about 100 and 250 cm².

In some cases, the electrophoresis apparatus can have a small total volume. The total volume of the electrophoresis apparatus can be less than or equal to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20 liters. The total volume of the electrophoresis apparatus can be between about 1 liter and about 10 liters. The total volume of the electrophoresis apparatus can be between about 1 liter and about 5 liters. The total volume of the electrophoresis apparatus can be between about 1 liter and about 3.5 liters.

In some cases, the electrophoresis apparatus can be portable. The electrophoresis apparatus can be sized to be capable of being carried by a human. The electrophoresis apparatus can be sized to be capable of being carried in one hand. The electrophoresis apparatus can be handheld.

Control Systems

The present disclosure provides computer control systems that are programmed to implement methods of the disclosure. FIG. 24 shows a computer system 2401 that is programmed or otherwise configured to perform electrophoresis. The computer system 2401 can regulate various aspects of electrophoresis processes of the present disclosure, such as, for example: operational voltage or field strength; operational running time; imaging or detection of electrophoresis processes and products; receipt, logging, and transmission of operational instructions; receipt, logging, and transmission of operational data; and recording, processing, or transmission of imaging or detection data.

The computer system 2401 includes a central processing unit (CPU, also "processor" and "computer processor" herein) 2405, which can be a single core or multi core processor, or a plurality of processors for parallel processing. The computer system 2401 also includes memory or memory location 2410 (e.g., random-access memory, read-only memory, flash memory), electronic storage unit 2415 (e.g., hard disk), communication interface 2420 (e.g., network adapter) for communicating with one or more other systems, and peripheral devices 2425, such as cache, other memory, data storage and/or electronic display adapters. The memory 2410, storage unit 2415, interface 2420 and peripheral devices 2425 are in communication with the CPU 2405 through a communication bus (solid lines), such as a motherboard. The storage unit 2415 can be a data storage unit (or data repository) for storing data. The computer system 2401 can be operatively coupled to a computer network ("network") 2430 with the aid of the communication interface 2420. The network 2430 can be the Internet, an internet and/or extranet, or an intranet and/or extranet that is in communication with the Internet. The network 2430 in some cases is a telecommunication and/or data network. The network 2430 can include one or more computer servers, which can enable distributed computing, such as cloud computing. The network 2430, in some cases with the aid of the computer system 2401, can implement a peer-to-peer network, which may enable devices coupled to the computer system 2401 to behave as a client or a server.

The CPU 2405 can execute a sequence of machine-readable instructions, which can be embodied in a program or software. The instructions may be stored in a memory location, such as the memory 2410. Examples of operations performed by the CPU 2405 can include fetch, decode, execute, and writeback.

The CPU 2405 can be part of a circuit, such as an integrated circuit. One or more other components of the system 2401 can be included in the circuit. In some cases, the circuit is an application specific integrated circuit (ASIC).

The storage unit 2415 can store files, such as drivers, libraries and saved programs. The storage unit 2415 can store user data, e.g., user preferences and user programs. The computer system 2401 in some cases can include one or more additional data storage units that are external to the computer system 2401, such as located on a remote server that is in communication with the computer system 2401 through an intranet or the Internet.

The computer system 2401 can communicate with one or more remote computer systems through the network 2430. For instance, the computer system 2401 can communicate with a remote computer system of a user (e.g., operator). Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants. The user can access the computer system 2401 via the network 2430.

Methods as described herein can be implemented by way of machine (e.g., computer processor) executable code stored on an electronic storage location of the computer system 2401, such as, for example, on the memory 2410 or electronic storage unit 2415. The machine executable or machine readable code can be provided in the form of software. During use, the code can be executed by the processor 2405. In some cases, the code can be retrieved from the storage unit 2415 and stored on the memory 2410 for ready access by the processor 2405. In some situations, the electronic storage unit 2415 can be precluded, and machine-executable instructions are stored on memory 2410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2401 can include or be in communication with an electronic display that comprises a user interface (UI) for providing, for example, voltage readings. Examples of UIs include, without limitation, a text interface, a graphical user interface (GUI) and web-based user interface.

Methods and systems of the present disclosure can be implemented by way of one or more algorithms. An algorithm can be implemented by way of software upon execution by one or more computer processors. In some examples, an algorithm for image processing comprises quadratic filters, Kalman filters, or correction of aberrations or distortions (e.g., fisheye correction).

Control systems can interact with components of the apparatus or detector by means of electrical or electronic signals. Signals can comprise instructions to one or more components. Signals can control the output voltage from a power supply circuit or an input voltage to electrodes. Signals can turn the power supply on or off. Signals can control the intensity, brightness, wavelength, or on/off status of a light source. Signals can control a detector to turn it on or off, adjust the frame rate, adjust exposure settings, or take an image. Signals can control communication equipment to send or receive information, images, operational data, or instructions. Communication equipment can send signals to control systems, causing instructions or controls to be performed on other elements of the apparatus or detector. A detector can send signals comprising images to control systems or communications equipment. Apparatus elements can send signals comprising operational data to control systems or communications equipment.

As noted herein, the devices described herein can provide several advantages. For example, low voltage and/or power requirements can allow the apparatus to be portable. Low voltage and/or power requirements can allow the apparatus to be operated in settings where other electrophoresis apparatuses could not be operated. For example, electrophoresis apparatuses with low voltage and/or power requirements can be operated outside of a laboratory setting, such as in a motor vehicle (e.g., a car), in a medical patient's residence, or at a sampling site (e.g., an environmental sampling site such as a river).

Communication equipment used with or integrated into the electrophoresis apparatus can allow remote monitoring and operation of an electrophoresis apparatus. Remote monitoring and operation can permit the processing of samples at multiple sites by a reduced number of technicians or personnel. Remote monitoring and operation can allow analysis or interpretation of results by personnel not present on site, in real time or after operation. Remote monitoring and operation can allow images and data to be backed up or stored remotely.

EXAMPLES

Example 1

Operation from Motor Vehicle Power

A user takes an electrophoresis apparatus into a motor vehicle. The user plugs the power supply of the electrophoresis apparatus into the cigarette lighter power adaptor of the motor vehicle. The user adds electrophoresis gel to the electrophoresis apparatus, and loads samples and buffer into the electrophoresis apparatus. The user sets the electrophoresis apparatus to run. The electrophoresis apparatus draws power from the motor vehicle and produces an electric field for electrophoresis. The samples are separated and the results of the electrophoresis are recorded.

Example 2

Multiple Gel Types

A user takes an electrophoresis apparatus and loads a gel comprising multiple lanes. Some of the lanes comprise 6% polyacrylamide and some of the lanes comprise 12% polyacrylamide. Samples are loaded into wells corresponding to the lanes. An electrophoretic separation is performed. Sample components are separated with higher resolution over a wider range of molecule sizes than if they had been run in gel lanes of a single composition.

Example 3

Simultaneous Loading

A user takes an electrophoresis apparatus and loads a gel with sample loading wells. The sample loading wells are spaced apart to match the spacing of a multi-pipette. The user loads a sample into the multi-pipette. The user uses the multi-pipette to load the sample into multiple wells on the gel simultaneously.

Example 4

Remote Monitoring

A user loads a gel into an electrophoresis apparatus, and loads samples into the gel. The user initiates an electrophoretic separation with the electrophoresis apparatus. The user travels to a separate location from the electrophoresis apparatus. Live images of the progress of the separation are viewed by the user on a remote monitoring device.

Example 5

Remote Control

A user loads a gel into an electrophoresis apparatus, and loads samples into the gel. The user initiates an electrophoretic separation with the electrophoresis apparatus. The user travels to a separate location from the electrophoresis apparatus. The user sends commands or instructions to the electrophoresis apparatus from a remote device, instructing it to stop the separation.

What is claimed is:

1. An apparatus for performing electrophoresis on a sample comprising:
   a frame comprising a bottom plate and a plurality of side walls and a least one lane separator; and
   an electrophoresis gel retained in said frame,
   wherein said at least one lane separator separates at least a portion of said electrophoresis gel from another portion of said electrophoresis gel into multiple lanes and inhibits transport of sample material between adjacent lanes during electrophoresis,
   wherein said at least one lane separator comprises a connector region, through which at least some of said sample can be transported between adjacent lanes, and
   wherein top surfaces of said electrophoresis gel in said multiple lanes are in fluid communication with one another.

2. The apparatus of claim 1, wherein said frame comprises a plurality of lane separators that are substantially parallel to each other.

3. The apparatus of claim 1, wherein said lane separator extends at least about 50% of the length of said electrophoresis gel.

4. The apparatus of claim 1, further comprising a detector configured to detect a signal from said electrophoresis gel while an electric field is applied to the electrophoresis gel.

5. The apparatus of claim 4, wherein said detector is configured to communicate wirelessly with an external device.

6. The apparatus of claim 1, wherein said lane separator is substantially parallel to at least one side wall of said plurality of side wells.

7. The apparatus of claim 1, wherein said frame comprises a plurality of lane separators that are substantially parallel to each other.

8. The apparatus of claim 1, further comprising an electrical component configured to produce an electric field through said electrophoresis gel that causes at least a portion of the sample to migrate through said electrophoresis gel.

9. The apparatus of claim 8, wherein said electrical component is configured to be powered by no more than 12 volts.

10. The apparatus of claim 1, further comprising a housing within which said frame, said electrophoresis gel, and said at least one lane separator are contained.

11. The apparatus of claim 10, wherein said housing is configured to prevent external light from entering said housing.

12. The apparatus of claim 1, further comprising a light source.

13. An apparatus for performing electrophoresis on a sample comprising:
    a frame comprising a bottom plate and a plurality of side walls and a least one lane separator; and
    an electrophoresis gel retained in said frame,
    wherein the at least one lane separator separates at least a portion of said electrophoresis gel from another portion of said electrophoresis gel into multiple lanes and inhibits transport of sample material between adjacent lanes during electrophoresis,
    wherein said electrophoresis gel in a first lane of the multiple lanes varies in composition from said electrophoresis gel in a second lane of said multiple lanes, and
    wherein top surfaces of said electrophoresis gel in said multiple lanes are in fluid communication with one another.

14. The apparatus of claim 13, wherein said frame comprises a plurality of lane separators that are substantially parallel to each other.

15. The apparatus of claim 13, wherein said lane separator extends at least about 50% of the length of said electrophoresis gel.

16. The apparatus of claim 13, further comprising a detector configured to detect a signal from said electrophoresis gel while an electric field is applied to the electrophoresis gel.

17. The apparatus of claim 16, wherein said detector is configured to communicate wirelessly with an external device.

18. The apparatus of claim 13, wherein said lane separator is substantially parallel to at least one side wall of said plurality of side wells.

19. The apparatus of claim 13, wherein said frame comprises a plurality of lane separators that are substantially parallel to each other.

20. The apparatus of claim 13, further comprising an electrical component configured to produce an electric field through said electrophoresis gel that causes at least a portion of the sample to migrate through said electrophoresis gel.

21. The apparatus of claim 20, wherein said electrical component is configured to be powered by no more than 12 volts.

22. The apparatus of claim 13, further comprising a housing within which said frame, said electrophoresis gel, and said at least one lane separator are contained.

23. The apparatus of claim 22, wherein said housing is configured to prevent external light from entering said housing.

24. The apparatus of claim 13, further comprising a light source.

* * * * *